US012805853B2

(12) United States Patent
Eidenschink et al.

(10) Patent No.: US 12,805,853 B2
(45) Date of Patent: Nov. 24, 2026

(54) MEDICAL DEVICE FOR CLOSURE OF A VASCULAR ABNORMALITY

(71) Applicant: St. Jude Medical, Cardiology Division, Inc., St. Paul, MN (US)

(72) Inventors: Tracee Eidenschink, Wayzata, MN (US); Theodore P. Dale, Corcoran, MN (US); Philip Osterbauer, Wyoming, MN (US); Linda Cornelius, Wayzata, MN (US); Andrea Stafford, New Brighton, MN (US); Kristopher Vietmeier, Monticello, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 0 days.

(21) Appl. No.: 17/538,224

(22) Filed: Nov. 30, 2021

(65) Prior Publication Data

US 2022/0167955 A1 Jun. 2, 2022

Related U.S. Application Data

(60) Provisional application No. 63/120,035, filed on Dec. 1, 2020.

(51) Int. Cl.
*A61B 17/00* (2006.01)
*A61B 17/12* (2006.01)

(52) U.S. Cl.
CPC ...... *A61B 17/0057* (2013.01); *A61B 17/1214* (2013.01); *A61B 17/12168* (2013.01);
(Continued)

(58) Field of Classification Search
CPC ............ A61B 17/0057; A61B 17/1214; A61B 17/12168; A61B 2017/00584;
(Continued)

(56) References Cited

U.S. PATENT DOCUMENTS

| | | | | |
|---|---|---|---|---|
| 8,777,974 B2 * | 7/2014 | Amplatz | .......... | A61B 17/12159 606/200 |
| 2003/0028213 A1 * | 2/2003 | Thill | .................. | A61B 17/0057 606/200 |
| 2003/0225421 A1 * | 12/2003 | Peavey | ............. | A61B 17/0057 606/151 |
| 2006/0122680 A1 * | 6/2006 | Auth | .................. | A61B 18/1492 607/122 |

(Continued)

OTHER PUBLICATIONS

European Search Report and Preliminary Opinion for related EP Patent Application No. 21211349.2, mailed Apr. 29, 2022, 10 pages.

*Primary Examiner* — Kathleen S Holwerda
*Assistant Examiner* — James R McGinnity
(74) *Attorney, Agent, or Firm* — SLEMAN & LUND LLP

(57) ABSTRACT

A medical device includes a central segment proximate a middle of the medical device a terminus proximate the middle of the medical device and spaced from the central segment in a depthwise direction. The medical device includes a pair of inner reverse bends spaced from the central segment by a first body plane extending from the central segment to the pair of inner reverse bends in a first longitudinal direction, and a pair of outer reverse bends. The outer reverse bends are spaced from the pair of inner reverse bends by a second body plane extending from the pair of inner reverse bends to the pair of outer reverse bends in a second, opposite longitudinal direction, and the outer reverse bends are spaced from the terminus of the medical device by a third body plane extending in the first direction from the outer reverse bends to the terminus.

21 Claims, 30 Drawing Sheets

(52) U.S. Cl.
CPC ............... *A61B 2017/00584* (2013.01); *A61B 2017/00867* (2013.01); *A61B 2017/12054* (2013.01)

(58) Field of Classification Search
CPC ........... A61B 2017/00867; A61B 2017/12054; A61B 2017/00575; A61B 17/12022; A61B 2017/12031; A61B 1/00135; A61B 2017/00597; A61B 17/00615; A61B 2017/00601
See application file for complete search history.

(56) References Cited

U.S. PATENT DOCUMENTS

| | | | | | |
|---|---|---|---|---|---|
| 2007/0073337 | A1* | 3/2007 | Abbott | A61B 17/0057 | 606/213 |
| 2007/0282352 | A1* | 12/2007 | Carley | A61B 17/068 | 606/142 |
| 2007/0293889 | A1* | 12/2007 | Corcoran | A61B 17/0057 | 606/213 |
| 2011/0066180 | A1* | 3/2011 | Zeng | A61B 17/0057 | 606/213 |
| 2014/0257373 | A1* | 9/2014 | Prom | A61B 17/12031 | 606/213 |
| 2016/0045165 | A1* | 2/2016 | Braido | A61F 2/2412 | 623/2.1 |
| 2021/0169495 | A1* | 6/2021 | Gorochow | A61B 17/12172 | |
| 2022/0160508 | A1* | 5/2022 | Miyashiro | A61F 2/2454 | |

* cited by examiner

MEDICAL DEVICE FOR CLOSURE OF A VASCULAR ABNORMALITY

CROSS-REFERENCE TO RELATED APPLICATIONS

This application claims the benefit of priority to U.S. Prov. Pat. App. No. 63/120,035, filed Dec. 1, 2020, which is incorporated by reference herein in its entirety.

BACKGROUND OF THE DISCLOSURE

A. Field of Disclosure

The present disclosure relates generally to medical devices that are used in the human body. In particular, the present disclosure is directed to a medical device for closure of a vascular abnormality by securing two pieces of vascular tissue together.

B. Background

Medical devices are used to treat a variety of different target sites in the body, including abnormalities, vessels, organs, openings, chambers, channels, holes, cavities, and the like. At least some medical devices are formed from shape-memory material in a braided web configuration. At least some of these devices are permanently implanted within a patient's body at a target site to achieve an occlusive function.

Percutaneous procedures are becoming more prevalent in the surgical field. At least some percutaneous procedures access the left atrium through the septal wall. Additionally, many patients (e.g., approximately 10-20% of the population) have patent foramen ovale (PFO), which can be closed at any age. Conventional devices for closing PFOs include, for example, a braided-web closure device that is implanted in the channel defined through the septal wall, with braided-web discs on each side of the PFO to anchor the closure device as well as block the flow of blood through the channel. If, in the future, the need arises to cross the septal wall in a patient with a previously-closed PFO (e.g., to treat atrial fibrillation) a physician may need to navigate through the discs of the braided-web closure device.

SUMMARY OF THE DISCLOSURE

The present disclosure is directed to a medical device. The medical device includes a first end, a second end, and a central segment proximate a middle of the medical device and about which the medical device is symmetrical. The medical device also includes a pair of inner reverse bends spaced from the central segment by a first body plane extending from the central segment to the pair of inner reverse bends in a first longitudinal direction, and a pair of outer reverse bends. The pair of outer reverse bends are spaced from the pair of inner reverse bends by a second body plane extending from the pair of inner reverse bends to the pair of outer reverse bends in a second, opposite longitudinal direction, and the pair of outer reverse bends are spaced from the first and second ends of the medical device by a third body plane extending in the first direction from the outer reverse bends to the first and second ends.

The present disclosure is also directed to a delivery system for delivering a medical device to a target site. The delivery system includes a medical device including a first end, a second end, and a central segment proximate a middle of the medical device and about which the medical device is symmetrical. The medical device also includes a pair of inner reverse bends spaced from the central segment by a first body plane extending from the central segment to the pair of inner reverse bends in a first longitudinal direction, and a pair of outer reverse bends. The pair of outer reverse bends are spaced from the pair of inner reverse bends by a second body plane extending from the pair of inner reverse bends to the pair of outer reverse bends in a second, opposite longitudinal direction, and the pair of outer reverse bends are spaced from the first and second ends of the medical device by a third body plane extending in the first direction from the outer reverse bends to the first and second ends. The delivery system also includes a delivery device coupled to the medical device, the delivery device including a catheter and a delivery cable, wherein the medical device is coupled to the delivery cable, and wherein the delivery cable is configured to be advanced through the catheter to deploy the medical device at the target site.

The present disclosure is further directed to a method for closing a Patent Foramen Ovale (PFO). The method includes providing a medical device including a first end, a second end, and a central segment proximate a middle of the medical device and about which the medical device is symmetrical. The medical device also includes a pair of inner reverse bends spaced from the central segment by a first body plane extending from the central segment to the pair of inner reverse bends in a first longitudinal direction, and a pair of outer reverse bends. The pair of outer reverse bends are spaced from the pair of inner reverse bends by a second body plane extending from the pair of inner reverse bends to the pair of outer reverse bends in a second, opposite longitudinal direction, and the pair of outer reverse bends are spaced from the first and second ends of the medical device by a third body plane extending in the first direction from the outer reverse bends to the first and second ends. The method also includes advancing the medical device to the PFO using a delivery system including a catheter and a delivery cable, positioning the medical device relative to the PFO to secure a septum primum and septum secundum together, and de-coupling the medical device from the delivery cable to deploy the medical device.

BRIEF DESCRIPTION OF THE DRAWINGS

Corresponding reference characters indicate corresponding parts throughout the several views of the drawings. It is understood that Figures are not necessarily to scale.

DETAILED DESCRIPTION OF THE DISCLOSURE

Figure 1:
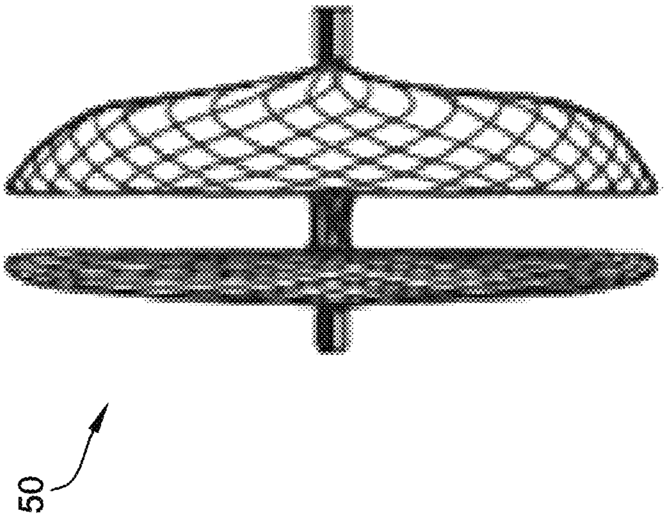
FIG. 1 (Prior Art)
FIG. 1 illustrates a known medical device utilized for occlusion.

The present disclosure relates generally to medical devices that are used in the human body. In particular, the present disclosure is directed to a medical device embodied as a clip configured to secure two pieces of tissue together. More specifically, the present disclosure is directed to a clip device that closes a patent foramen ovale (PFO) to facilitate proper blood flow within the heart while reducing an amount of material (e.g., providing a device without braided-web discs) to provide such closure. Accordingly, the medical devices of the present disclosure may enable an improvement in crossing the septal wall during future medical procedures while maintaining efficacy in closing the PFO.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

Although the exemplary embodiment of the medical device is described as treating a target site including a patent foramen ovale (PFO), it is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as a left atrial appendage (LAA), an atrial septal defect, a lesion, a vessel dissection, or a tumor. Embodiments of the medical device may be useful, for example, for occluding an atrial septal defect (ASD), ventricular septal defect (VSD), or patent ductus arteriosus (PDA). Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device.

The medical device may include a first end, a second end, a central segment proximate a middle of the medical device and about which the medical device may be symmetrical, a pair of inner reverse bends spaced from the central segment by a first body plane extending from the central segment to the pair of inner reverse bends in a first longitudinal direction, and a pair of outer reverse bends, wherein the pair of outer reverse bends are spaced from the pair of inner reverse bends by a second body plane extending from the pair of inner reverse bends to the pair of outer reverse bends in a second, opposite longitudinal direction, and wherein the pair of outer reverse bends are spaced from the first and second ends of the medical device by a third body plane extending in the first direction from the pair of outer reverse bends to the first and second ends. As described further herein, the inner reverse bends of the medical device are configured to engage the septum primum and the outer bends are configured to engage the septum secundum to substantially preclude or occlude the flow of blood by closing the PFO.

The present disclosure will now be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

In at least some conventional or known medical devices, such as a medical device 50 shown in FIG. 1, the medical device 50 is formed from shape-memory material in a braided configuration. These devices employ discs with a braided mesh configuration to facilitate thrombosis to seal a vascular abnormality. The collection of the thrombi in the mesh of the discs allows for the device to provide an occlusive effect. However, if the patient later requires a medical procedure that involves crossing over or through the implanted device, the physician must navigate through the braided material. This may increase the duration of a procedure and/or may adversely impact the sealing function of the medical device 50, which may require an additional or extended procedure to implant a new medical device.

The medical devices of the present disclosure enable the closure of an abnormality while reducing the amount of material implanted in the body, compared to known devices. Accordingly, the medical device of the present disclosure reduces or eliminates the above-described disadvantages of known medical devices while providing sufficient closure and sealing effect.

Figure 2:
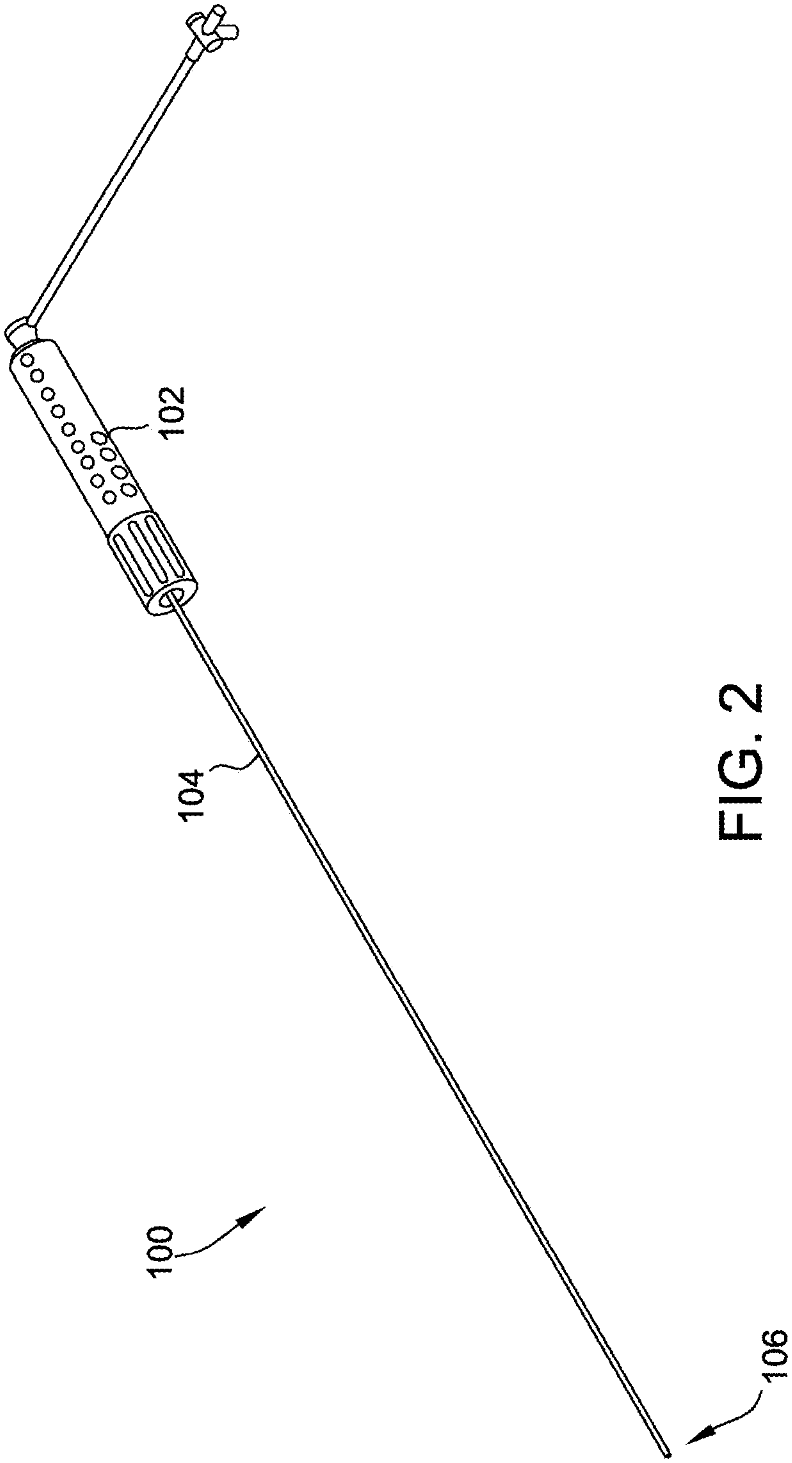
FIG. 2 is a schematic view of an exemplary embodiment of a delivery system for deploying a medical device.

Turning now to FIG. 2, a schematic diagram of a delivery system 100 is shown. Delivery system 100 includes a delivery device 102, such as a manifold or handle, that includes or is coupled to a catheter 104 and a delivery cable 106 for deployment of a medical device 108 (see FIG. 3) at a target site. Delivery system 100 may be a static, curved, and/or steerable device delivery system.

Figure 3:
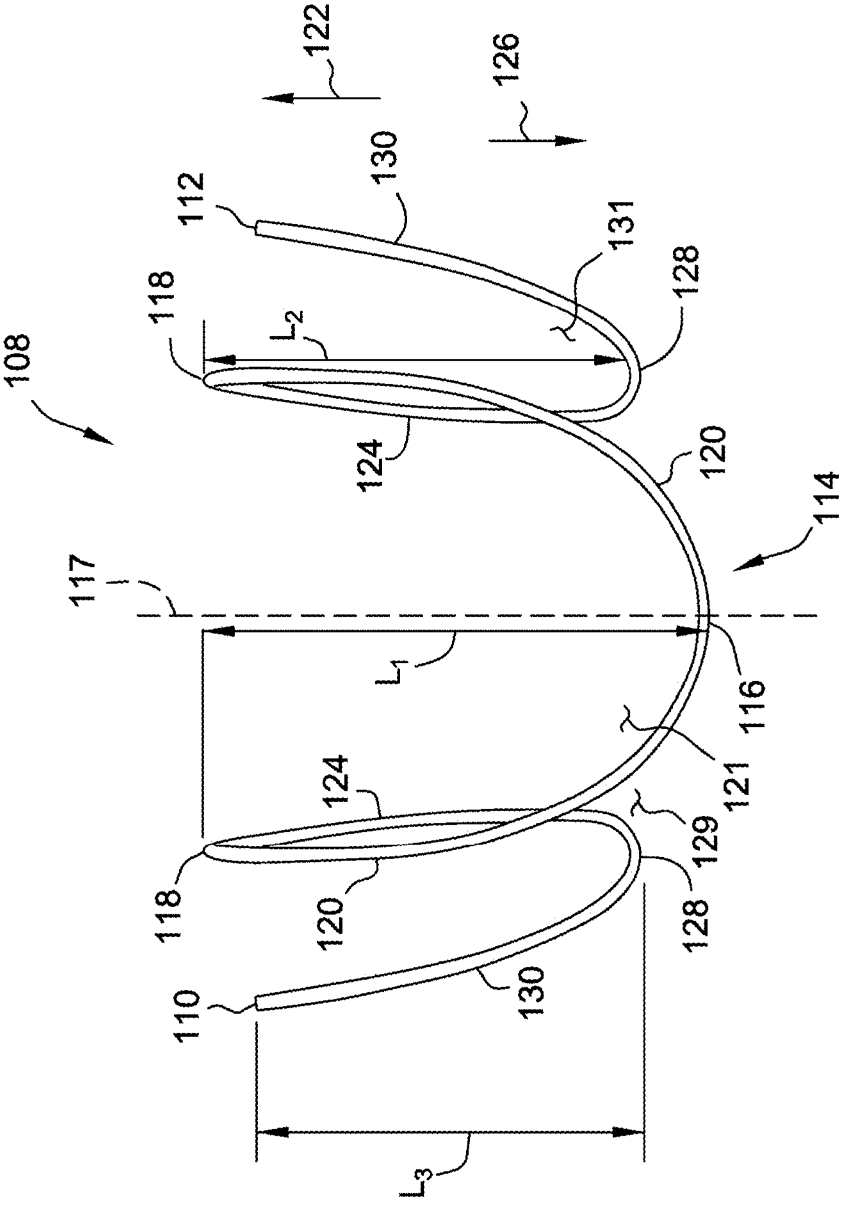
FIG. 3 is a front plane view of an exemplary embodiment of a medical device.
Figure 4:
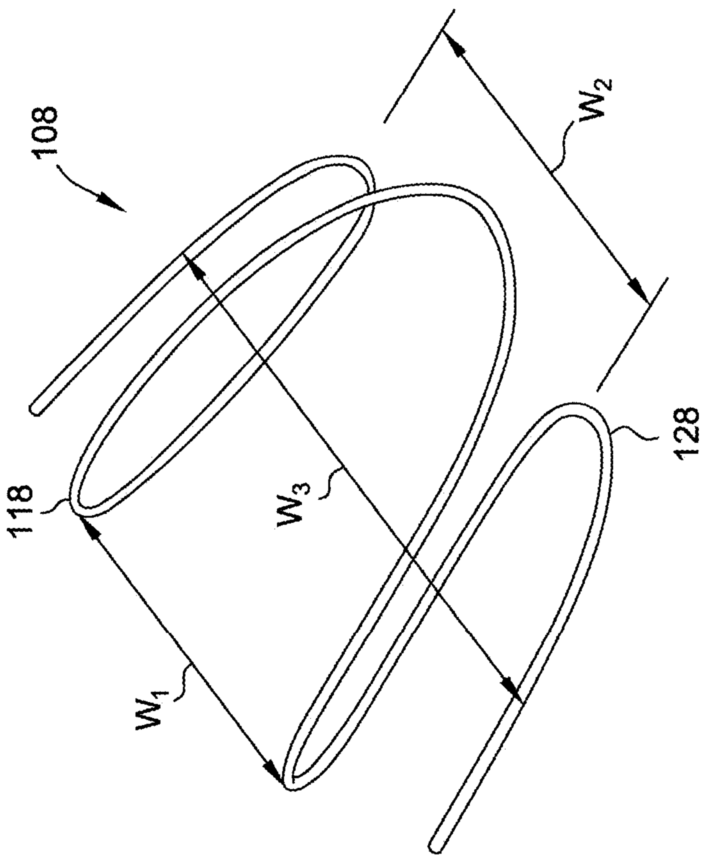
FIG. 4 is a front perspective view of the medical device shown in FIG. 3.
Figure 5:
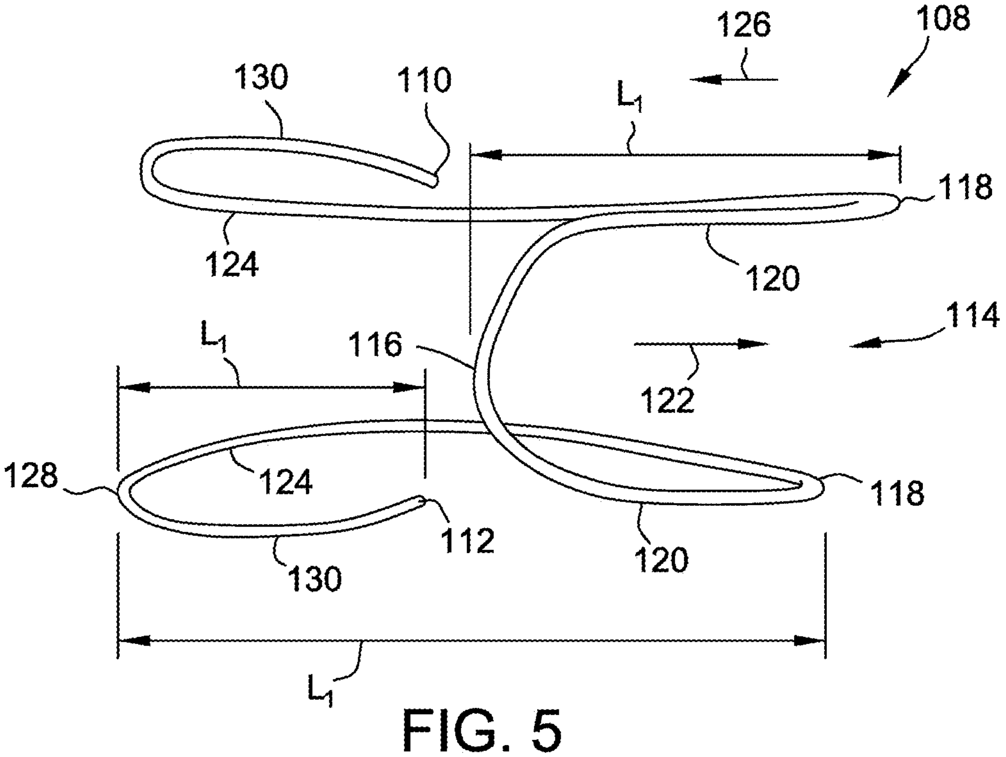
FIG. 5 is a perspective view of another embodiment of a medical device.
Figure 6:
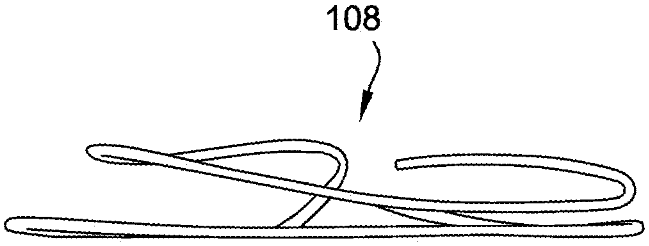
FIG. 6 is a side perspective view of the medical device shown in FIG. 5 after undergoing a heat-set process.
Figure 7:
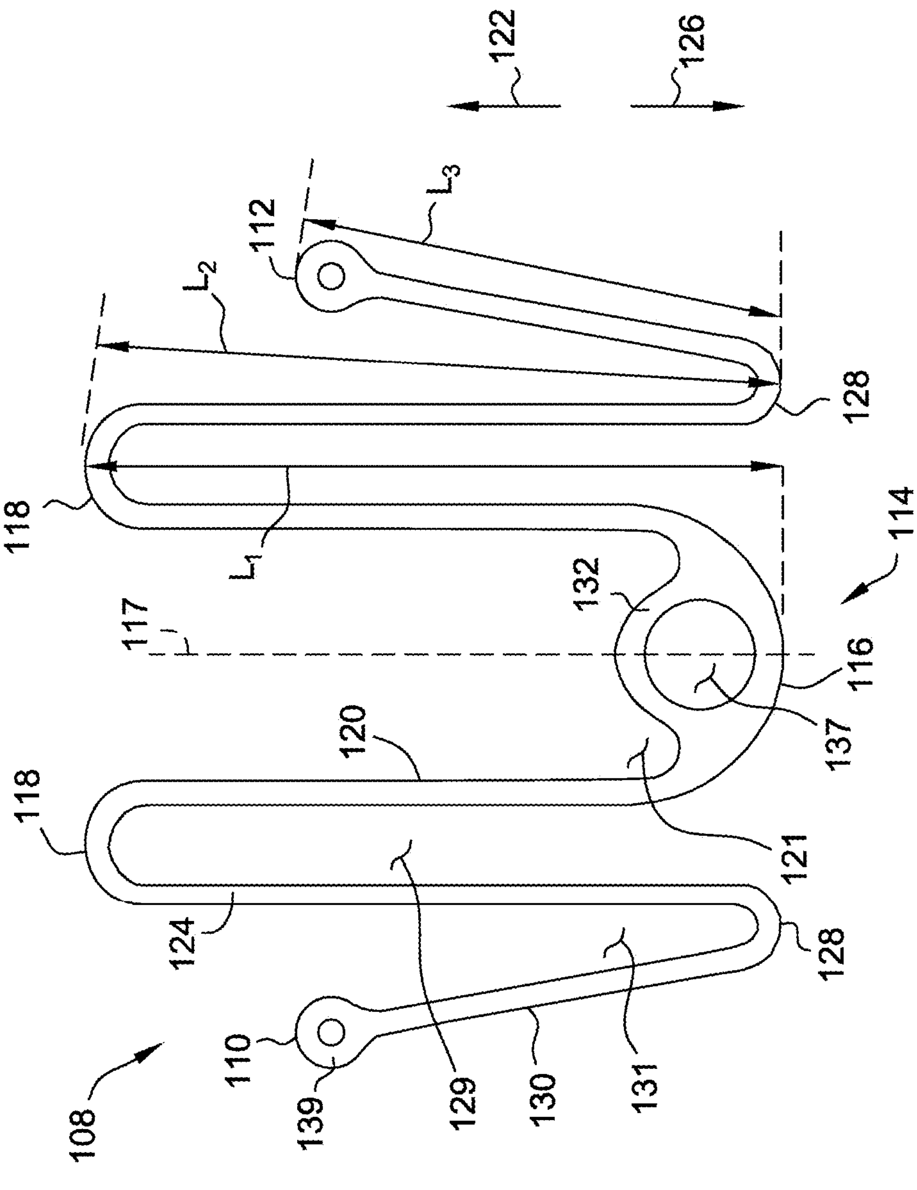
FIG. 7 is a front plane view of another embodiment of a medical device, illustrated in the form of a two-dimensional medical device.
Figure 8:
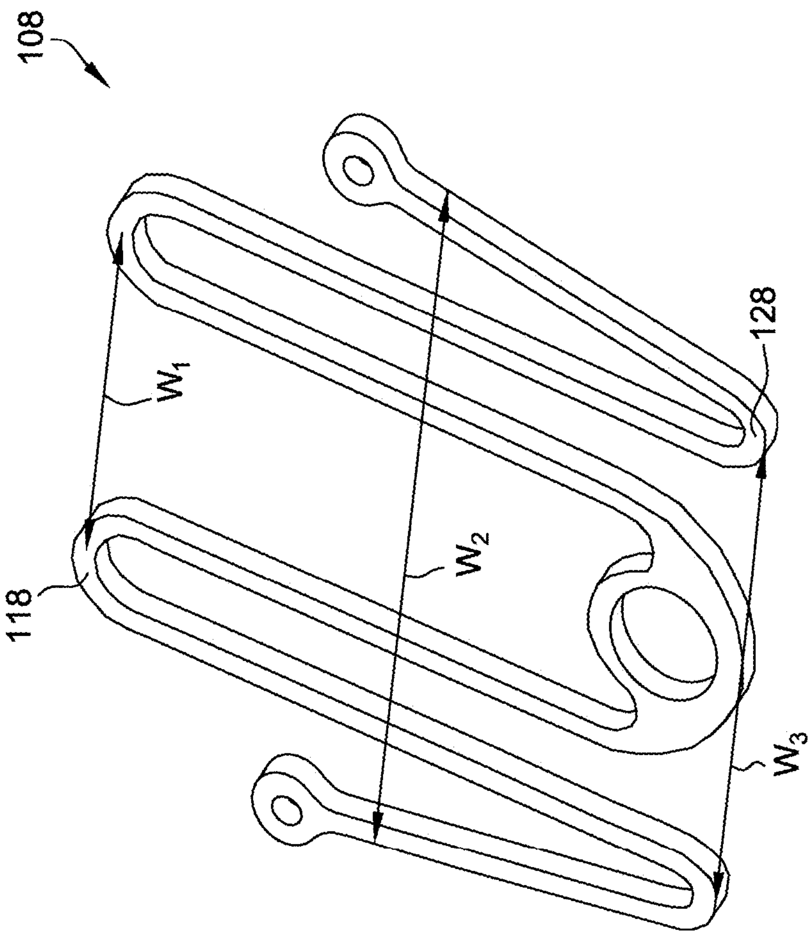
FIG. 8 is a front perspective view of the medical device shown in FIG. 7.
Figure 9:
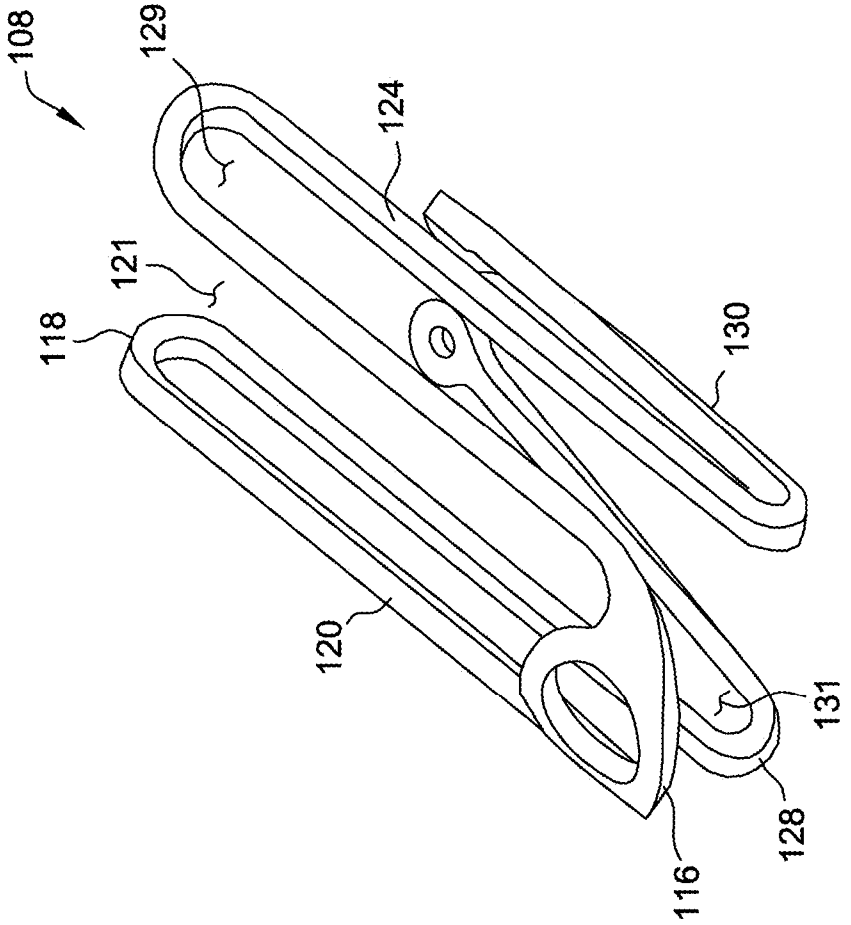
FIG. 9 is a front perspective view of another embodiment of a medical device, illustrated in the form of a three-dimensional medical device.
Figure 10:
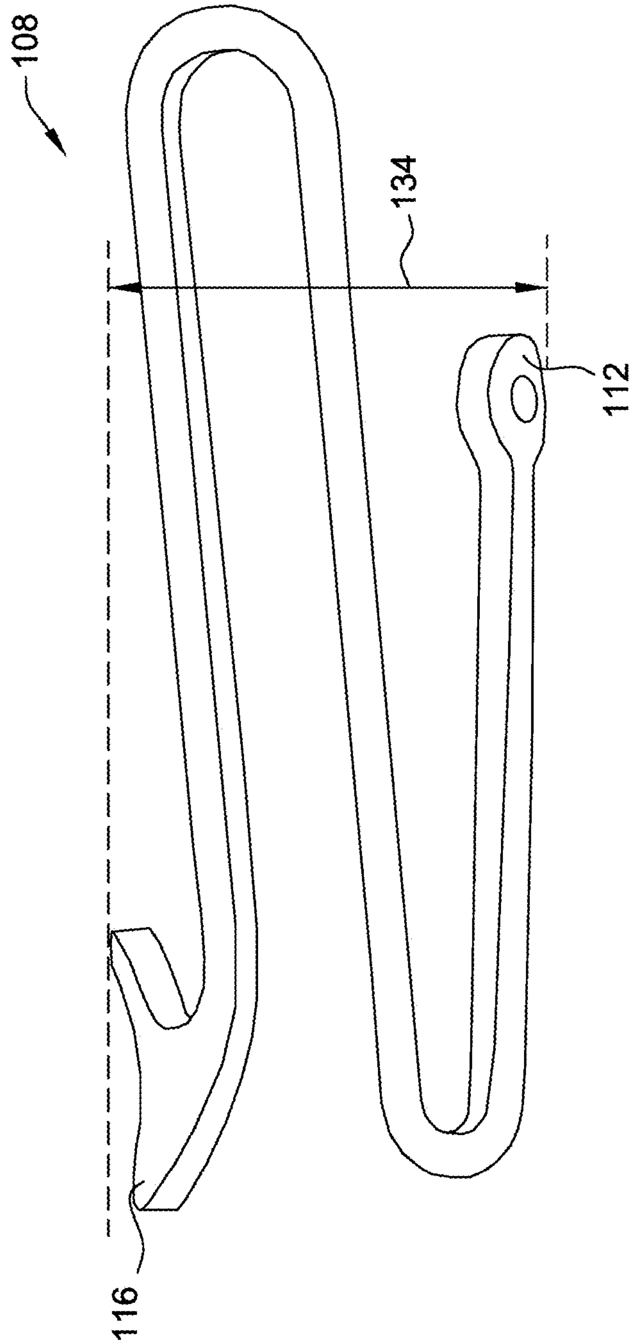
FIG. 10 is a side view of the medical device shown in FIG. 9.
Figure 11:
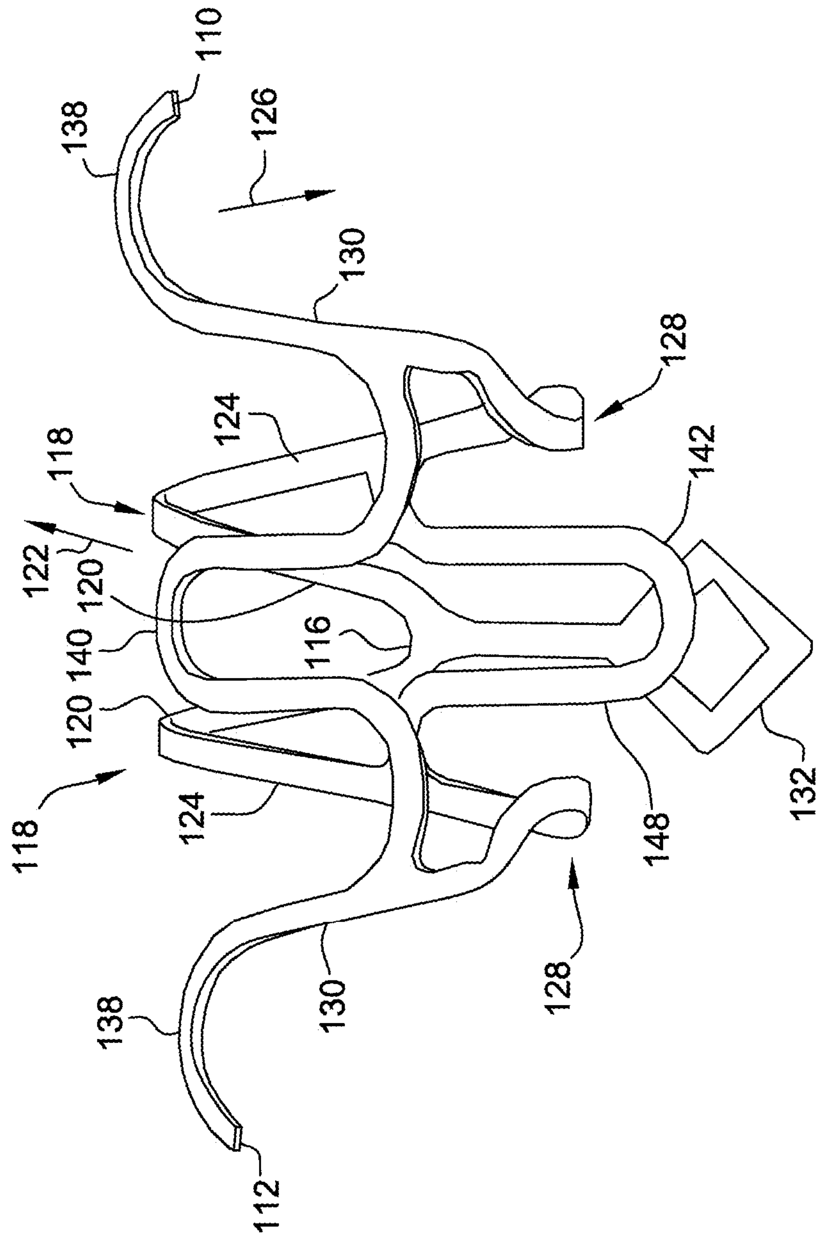
FIG. 11 is a back view of an embodiment of a medical device in a final or three-dimensional configuration.
Figure 12:
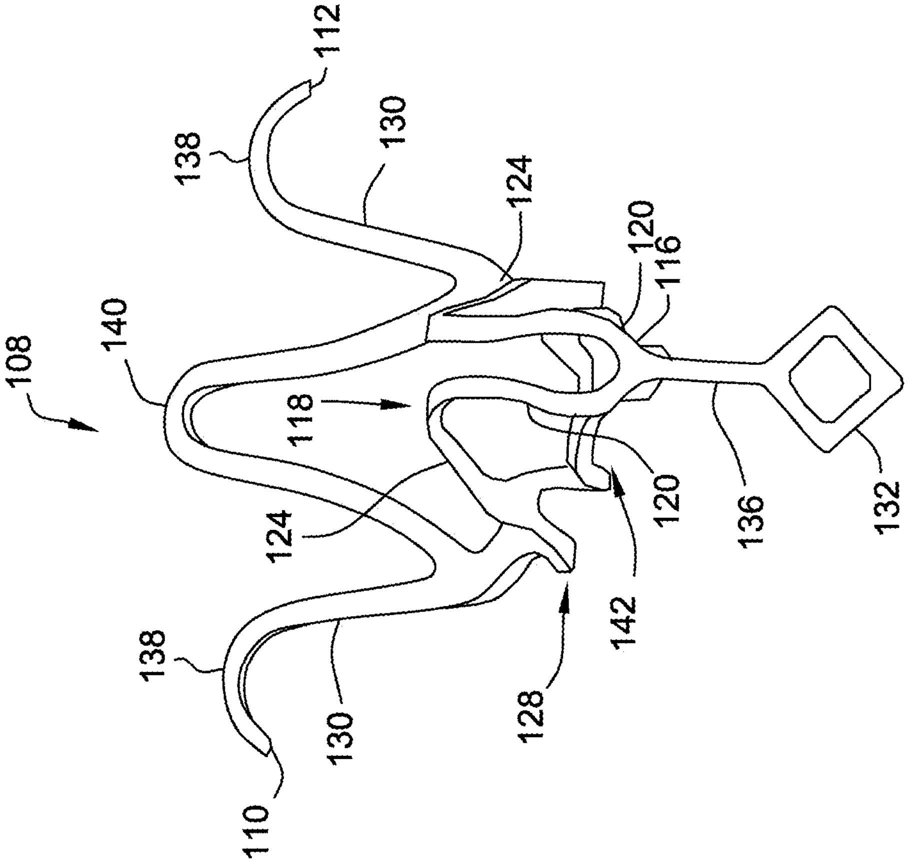
FIG. 12 is a front perspective view of another embodiment of a medical device in a final or three-dimensional configuration.
Figure 13:
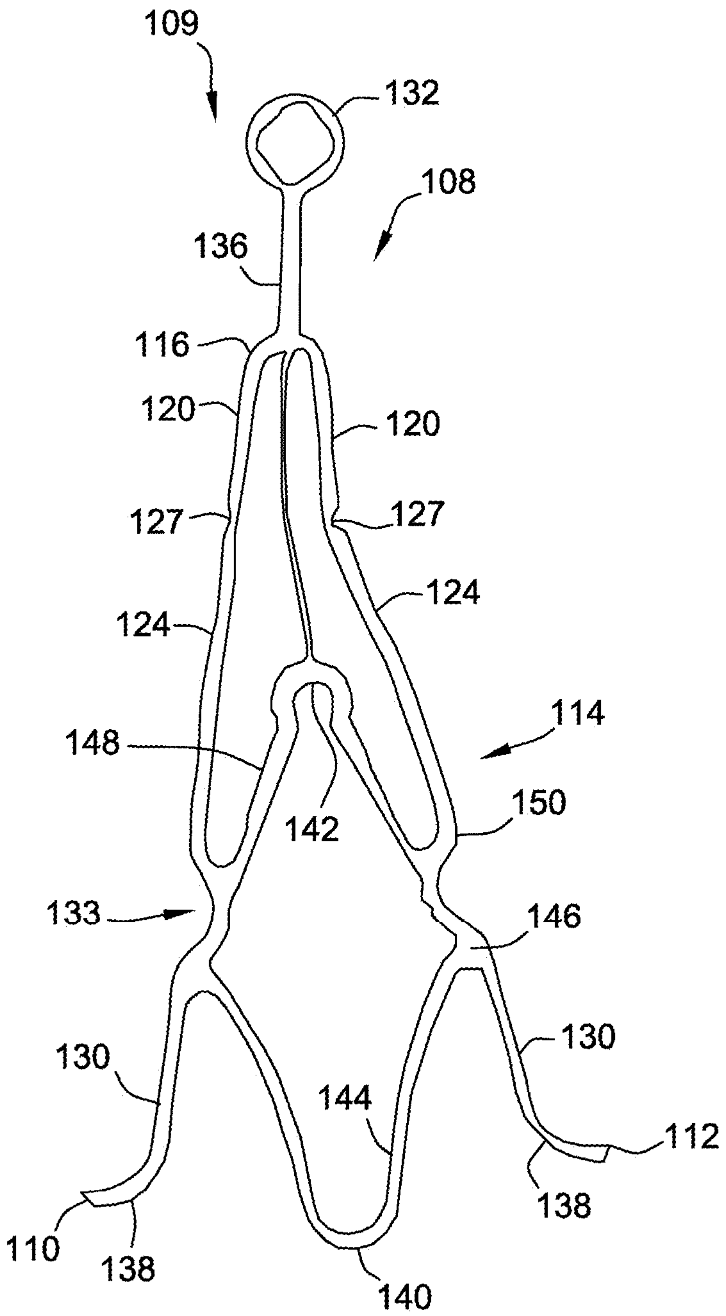
FIG. 13 is a front view of a blank for forming another embodiment of a medical device, or a medical device in an initial configuration.
Figure 14:
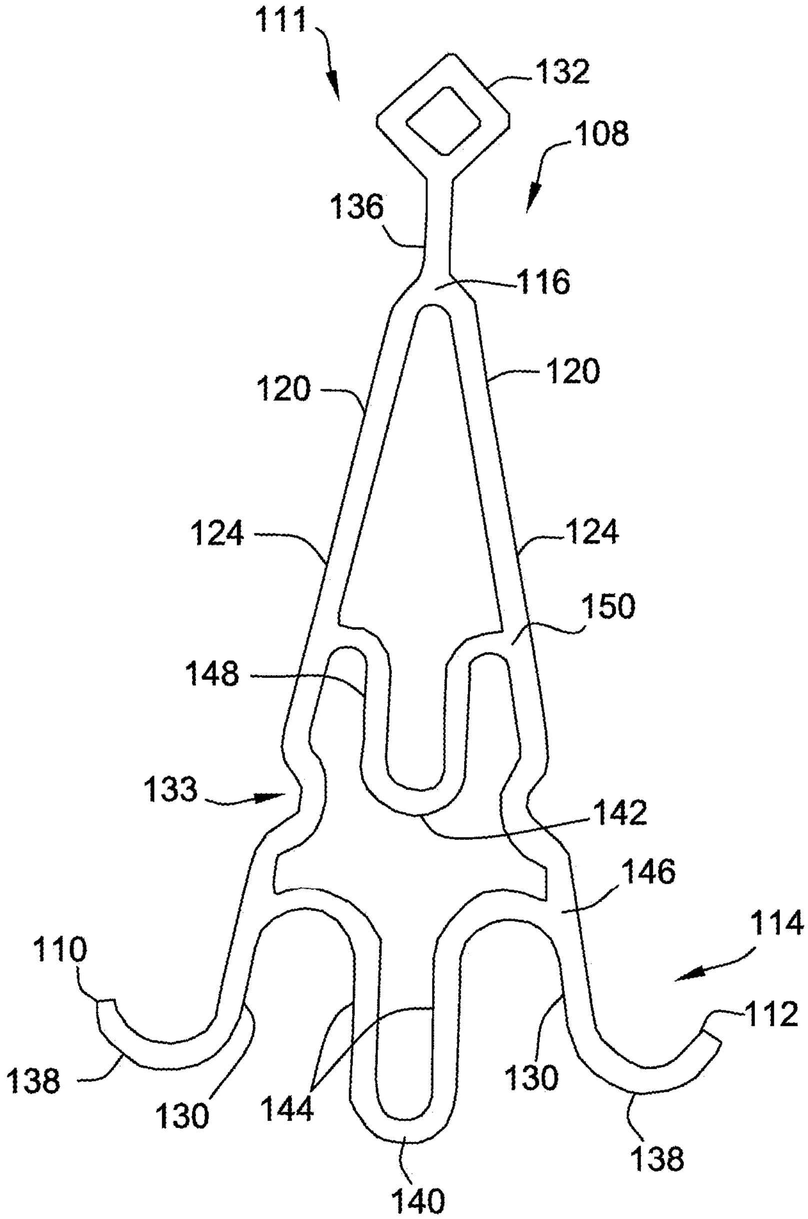
FIG. 14 is a front view of another blank for forming another embodiment of a medical device, or a medical device in an initial configuration.

FIGS. 3 and 4 depict a first exemplary embodiment of a medical device 108, FIGS. 5 and 6 depict a second exemplary embodiment of medical device, FIGS. 7-10 depict a third exemplary embodiment of medical device 108, FIG. 11 depicts a fourth exemplary embodiment of medical device 108, FIG. 12 depicts a fifth exemplary embodiment of medical device 108, and FIGS. 13 and 14 depict blanks 109 and 111, respectively, for forming medical devices 108 (e.g., medical devices 108 in an initial configuration, prior to being heat-set). With reference to FIGS. 3-14, medical device 108 includes a first end 110, a second end 112, and a body 114 that extends between first and second ends 110, 112. Medical device 108 may be referred to herein as a medical clip device, a clip device, and/or a clip.

Body 114 includes a central segment 116 that is proximate to a middle of body 114, or approximately equidistant from first end 110 and second end 112. Central segment 116 is located where a longitudinal axis 117 of medical device 108 intersects with body 114. Body 114 is generally symmetrical (e.g., U-shaped) about central segment 116 and/or longitudinal axis 117. In this embodiment, central segment 116 is embodied as an arc or curve through which body 114 is continuous.

Body 114 also includes a pair of inner reverse bends 118 that are approximately equidistant (laterally) from central segment 116 towards one of first and second ends 110, 112 of medical device 108. That is, body 114 is symmetrical about central segment 116 between inner reverse bends 118. As shown in FIGS. 3-14 (in particular in FIGS. 7-14), a pair of first legs 120 extends from central segment 116 to inner reverse bends 118. A first body plane 121 of medical device 108 is defined from central segment 116 to inner reverse bends 118, and between first legs 120, and represents a first plane of engagement between medical device 108 and tissue, when medical device 108 is deployed at a target site, as described further herein. First body plane 121 extends in a first longitudinal direction 122 from central segment 116 to inner reverse bends 118.

In the exemplary embodiment, first legs 120 extend linearly between central segment 116 to inner reverse bends 118; alternatively, first legs 120 may have any shape between central segment 116 and inner reverse bends 118. Moreover, first legs 120 are identical in the exemplary embodiment; alternatively, first legs 120 may be other than identical. Additionally, central segment 116 transitions smoothly (e.g., along an arcuate or curved path) to first legs 120, and first legs 120 transition smoothly (e.g., along an arcuate or curved path) to inner reverse bends 118.

First legs 120 extend in first longitudinal direction 122 from central segment 116 to inner reverse bends 118. At inner reverse bends 118, body 114 "reverses direction." Specifically, a pair of second legs 124 (which may be formed as an extension or second portion of first legs 120) extends in a second longitudinal direction 126, opposite to first longitudinal direction 122, from inner reverse bends 118. In some embodiments, as shown in FIG. 13, body 114 includes cutouts 127 that improve bending between first legs 120 and second legs 124 to form inner reverse bends 118. Cutouts 127 also reduce the stress generated between first legs 120 and second legs 124 during the bending to form second legs 124 (e.g., to reverse the body direction at inner reverse bends 118).

Body 114 also includes a pair of outer reverse bends 128. Each outer reverse bend 128 is approximately equidistant from a respective one of inner reverse bends 118, towards one of first and second ends 110, 112 of medical device 108. Second legs 124 extend (in second longitudinal direction 126) from inner reverse bends 118 to outer reverse bends 128. Body 114 is generally M-shaped (or W-shaped) and/or symmetrical about central segment 116 between outer reverse bends 128. A second body plane 129 of medical device 108 is defined from inner reverse bends 118 to outer reverse bends 128, and between second legs 124, and represents a second plane of engagement between medical device 108 and tissue, when medical device 108 is deployed at a target site, as described further herein. Second body plane 129 extends in second longitudinal direction 126 from inner reverse bends 118 to outer reverse bends 128.

In the exemplary embodiment, second legs 124 extend linearly from inner reverse bends 118 to outer reverse bends 128; alternatively, second legs 124 may have any shape between inner reverse bends 118 and outer reverse bends 128. Moreover, second legs 124 are identical in the exemplary embodiment; alternatively, second legs 124 may be other than identical. Additionally, inner reverse bends 118 transition smoothly (e.g., along an arcuate or curved path) to second legs 124, and second legs 124 transition smoothly (e.g., along an arcuate or curved path) to outer reverse bends 128.

First legs 120 have a first length $L_1$, defined between a maximum of central segment 116 and a maximum of a respective inner reverse bend 118. Second legs 124 have a second length $L_2$, defined between the maximum of a respective inner reverse bend 118 and a maximum of a respective outer reverse bend 128. In some embodiments, first length $L_1$ may be greater than second length $L_2$ (see, for example, FIGS. 3 and 4). In other embodiments, first length $L_1$ is less than second length $L_2$ (see FIGS. 5 and 6, and FIGS. 11 and 12). In still other embodiments, first length $L_1$ is substantially equal to second length $L_2$ (see, for example, FIGS. 7-10).

In the exemplary embodiment, a pair of third legs 130 extend from outer reverse bends 128, each third leg 130 extending (in first longitudinal direction 122) from one of outer reverse bends 128 to a respective one of first end 110 and second end 112 of medical device 108. That is, each third leg 130 terminates at one of first end 110 and second end 112. A third body plane 131 of medical device 108 is defined from outer reverse bends 128 to ends 110, 112, and between third legs 130, and represents a third plane of engagement between medical device 108 and tissue, when medical device 108 is deployed at a target site, as described further herein. Third body plane 131 extends in first longitudinal direction 122 from outer reverse bends 128 to ends 110, 112.

In the exemplary embodiment, third legs 130 extend linearly from outer reverse bends 128; alternatively, third legs 130 may have any shape between outer reverse bends 128 and first and second ends 110, 112. Moreover, third legs 130 are identical in the exemplary embodiment; alternatively, third legs 130 may be other than identical. Additionally, third legs 130 transition smoothly (e.g., along an arcuate or curved path) from outer reverse bends 128. In some embodiments, as shown in FIGS. 13 and 14, body 114 includes concave joints 133 that improve bending between second legs 124 and third legs 130, to form outer reverse bends 128.

Third legs 130 have a third length $L_3$, defined between the maximum of a respective outer reverse bend 128 and a respective one of first end 110 and second end 112. In some embodiments, third length $L_3$ is substantially equal to first length $L_1$ and/or second length $L_2$ (see, for example, FIGS. 3 and 4, in which third length is substantially equal to second length $L_2$). In other embodiments, third length $L_3$ is less than first length $L_1$ and second length $L_2$ (see, for example, FIGS. 5-10). Alternatively, third length $L_3$ may be greater than first length $L_1$ and/or second length $L_2$.

A first width $W_1$ (see FIGS. 4 and 8) is defined between inner reverse bends 118, and may be referred to as a width of first body plane 121. A second width $W_2$ is defined between outer reverse bends 128, and may be referred to as a width of second body plane 129. A third width $W_3$ or central width is defined at a transverse center of body 114, and may be referred to as a width of third body plane 131.

In one embodiment, medical device 108 is formed from a shape-memory material. One particular shape memory material that may be used is Nitinol. Nitinol alloys are highly elastic and are said to be "superelastic," or "pseudoelastic." This elasticity may allow medical device 108 to be resilient and return to a preset, expanded configuration for deployment following passage in a distorted form through delivery catheter 104. Further examples of materials and manufacturing methods for medical devices with shape memory properties are provided in U.S. Pat. No. 8,777,974, titled "Multi-layer Braided Structures for Occluding Vascular Defects" and filed on Jun. 21, 2007, which is incorporated by reference herein in its entirety.

It is also understood that medical device 108 may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, polyurethane, silicone, PTFE, polyolefins and ePTFE.

In some embodiments, as shown in FIGS. 3 and 4 as well as in FIGS. 5 and 6, medical device 108 is formed from a thin wire material. In other embodiments, as shown in FIGS. 7-10, medical device 108 is formed from a laser-cut material.

In some embodiments, body 114 is bent and/or heat-set to define the final or expanded configuration thereof. For example, FIG. 5 illustrates medical device 108 prior to being heat-set, and FIG. 6 illustrates the same medical device 108 after being heat-set into its final configuration. Likewise, medical device 108 shown in FIGS. 9 and 10 may represent a final configuration of medical device 108 shown in FIGS. 7 and 8, after being heat-set. Medical devices 108, or blanks 109 and 111, shown in FIGS. 13 and 14, respectively, may represent initial configurations of medical devices 108 that are heat-set to form medical devices 108 such as those shown in FIGS. 11 and 12.

It is contemplated that medical device 108 may be embodied as a two-dimensional device (see FIG. 6 as well as FIGS. 7 and 8, in which a laser-cut medical device 108 is substantially flat), or a three-dimensional device (see FIGS. 3 and 4, FIG. 5, as well as FIGS. 9-12). Where medical device 108 is three-dimensional, a depth 134 (see FIG. 10) thereof may be defined between first and second ends 110, 112 and central segment 116. In other embodiment, depth 134 is defined between other outer-most points of medical device 108.

In some embodiments, as shown in FIGS. 7-10, central segment 116 of body 114 includes a loop 132. Loop 132 defines a through-hole 137 that enables attachment of delivery cable 106 to medical device 108 for delivery of medical device 108 to a target site, as described further herein. In other embodiments, loop 132 is spaced from central segment 116 by an extension 136, as shown in FIGS. 11-14. Medical device 108 may include any additional or alternative attachment mechanism(s), such as a hook or fastener, at any location thereof, such as at central segment 116, inner reverse bends 118, outer reverse bends 128, and/or first and/or second ends 110, 112.

Moreover, loop 132 and/or extension 136 may increase a surface area of central segment 116, which may reduce the pressure exerted by central segment 116 on adjacent tissue (when medical device 108 is deployed). In some embodiments, each of first and second ends 110, 112 are rounded, and may also include a loop 139 (as shown in FIGS. 7-10) and/or a rounded extension 138 (as shown in FIGS. 11-14). Loops 139 and/or rounded extensions 138 may similarly decrease the pressure exerted by first and second ends 110, 112 on adjacent tissue. Moreover, loops 139 and/or rounded extensions 138 may provide less sharp or pointed ends 110, 112 of medical device 108, reducing a risk of damage to surrounding tissue during and/or after deployment of medical device 108.

In some embodiments, as shown in FIGS. 11-14, medical device 108 may include a secondary central segment 140 and/or a tertiary central segment 142 (e.g., where central segment 116 is a "primary central segment"). More particularly, fourth legs 144 extend from first junctions 146 formed with third legs 130. Fourth legs 144 extend from first junctions 146 to secondary central segment 140, which is also located proximate to a middle of medical device 108 (like primary central segment 116). Secondary central segment 140 may increase a surface area of medical device 108 that engages with the outer side of the septum primum, within third body plane 131, as described further herein, to improve the stability of medical device 108 and to spread out the force applied by medical device 108 (e.g., by third body plane 131) along the outer side of the septum primum.

Fifth legs 148 extend from second junctions 150 formed with second legs 124. In some embodiments, as shown in FIG. 13, fifth legs 148 extend away from second junctions 150 to tertiary central segment 142 such that tertiary central segment 142 is oriented in a same direction as primary central segment 116. In other embodiments, as shown in FIG. 14, fifth legs 148 extend away from second junctions 150 to tertiary central segment 142 such that tertiary central segment 142 is oriented in an opposite direction from primary central segment 116. In such embodiments, as shown in FIG. 11, when blank 111 is used to form medical device 108 (e.g., when medical device 108 is in the final configuration), tertiary central segment 142 is parallel to and extends in a same direction as primary central segment 116. Tertiary central segment 142 may increase a surface area of medical device 108 that engages tissue between the septum primum and the septum secundum, within second body plane 129, which may improve the stability of medical device 108. Additionally or alternatively, tertiary central segment 142 may be partially curved to engage with an edge of the septum primum (e.g., along with outer reverse bends 128), which may spread out the force applied by medical device 108 (e.g., by second body plane 129) along the edge of the septum primum.

In operation, medical device 108 is advanced towards the target site within catheter 104 of delivery device 102. The distal end of the delivery device 102 can be configured to engage with the septum secundum or and/the septum premium. Once catheter 104 is advanced to the target, medical device 108 is deployed from catheter 104 using delivery cable 106. In some embodiments, medical device 108 is deployed into an abnormality to be occluded. Delivery cable 106 (or any other component of delivery system 100) facilitates positioning and/or orienting medical device 108 into a desired position at the target site. In one particular embodiment, for example, where medical device 108 is used to occlude a PFO (see FIGS. 15A-15C), ends 110, 112 and third legs 130 (e.g., third body plane 131) are first positioned in engagement with the right atrial side of the septum primum. Further, second legs 124 (e.g., second body plane 129) are positioned between the right atrial side of the septum secundum and the left atrial side of the septum primum, and outer reverse bends 128 engage with and hold the septum primum flap. Central segment 116 and first legs 120 (e.g., first body plane 121) are positioned into engagement with the right atrial side of the septum secundum, and an edge of the septum secundum is positioned against inner reverse bends 118. The placement and positioning of medical device 108 may be assessed and confirmed (e.g., by a physician) prior to disconnecting delivery cable 106 of delivery device 102 from the medical device 108.

Further, in some embodiments, delivery device 102 can be configured to allow manipulation (e.g., deflection in a proximal or distal direction) of either the septum secundum or the septum primum, for example, to facilitate positioning medical device 108 relative to the septum secundum and/or the septum primum.

Catheter 104 of the delivery system 100 may have any suitable size that enables medical device 108 and delivery system 100 to function as described herein. In some embodiments, the outer diameter of catheter 104 is about 8-12 French.

Figure 15A:
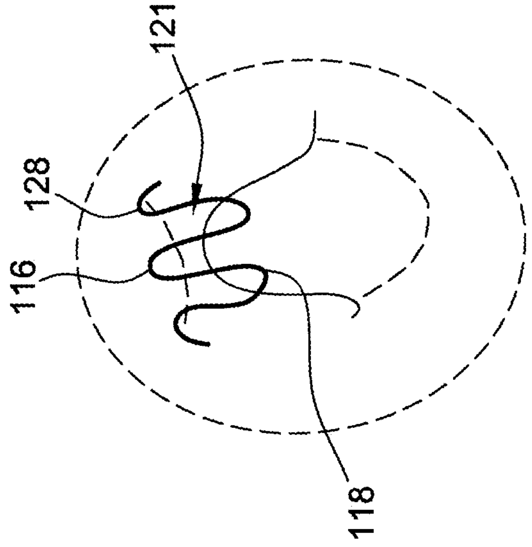
FIGS. 15A-15C depict a medical device deployed for closure of cardiac tissue.
Figure 15B:
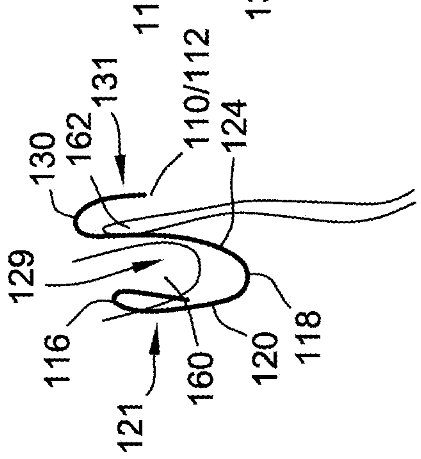
Figure 15C:
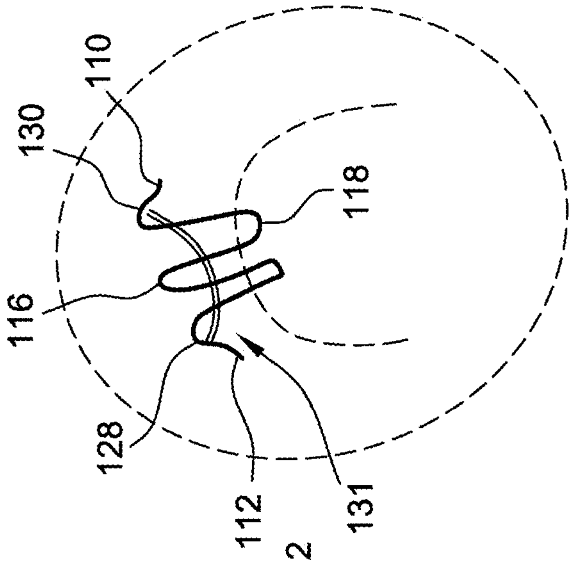

FIGS. 15A-15C illustrate medical device 108 in a deployed state. FIG. 15A is a right atrial view, FIG. 15B is a side view, and FIG. 15C is a left atrial view of medical device 108 in the deployed state. As shown in FIGS. 15A-15C, inner reverse bends 118 (e.g., first body plane 121) engage the septum secundum 160, and outer reverse bends 128 (e.g., third body plane 131) engage the septum primum 162. This configuration allows for the septum secundum 160 and septum primum 162 to engage with each other and close the abnormality, allowing for proper blood flow during the cardiac cycle. The distance between first end 110 and second end 112 is dependent upon the size of the opening to be occluded. The central width $W_3$ of medical device 108 is selected to hold the septum primum 162 taut during the cardiac cycle.

Figure 17:
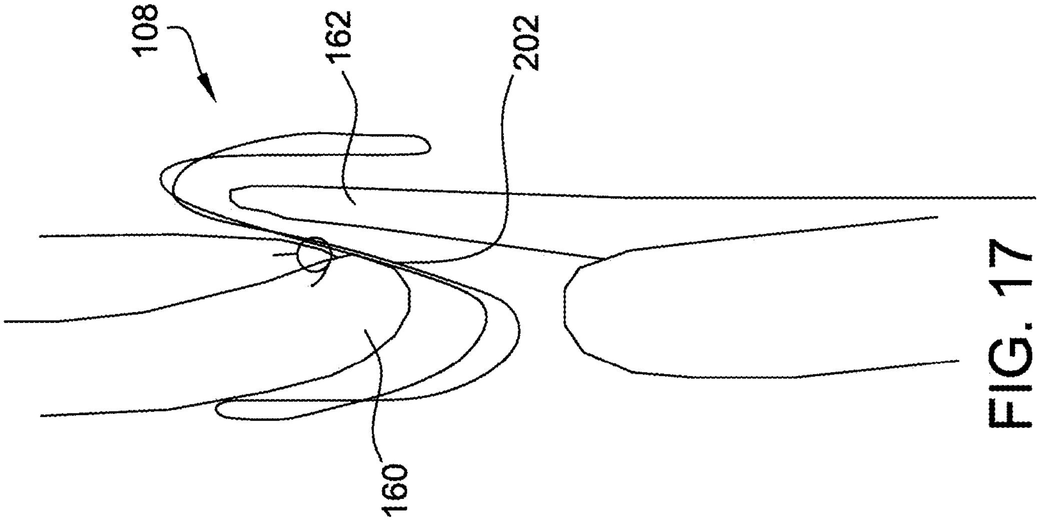
FIG. 17 depicts the medical device of FIGS. 16A and 16B deployed for closure of cardiac tissue.
Figure 16A:
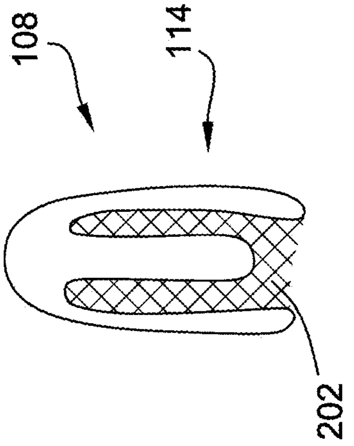
FIGS. 16A and 16B depict a top and side view of another embodiment of a medical device, including a bioadhesive material.
Figure 16B:
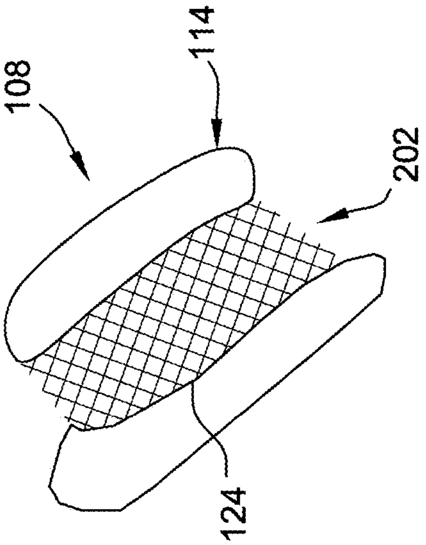

FIGS. 16A and 16B depict another embodiment of a medical device in accordance with the present disclosure. Specifically, FIG. 16A is a top view and FIG. 16B is a side view of a medical device 108 substantially similar to medical device 108 shown in FIGS. 3-6, further including a filler material 202 (shown in cross-hatching) coupled to body 114 of medical device 108. When medical device 108 is deployed in a PFO, as shown in FIG. 17, filler material 202 may fill the PFO tunnel and/or function as an adhesive to couple the septum secundum 160 and septum primum 162 together, and may facilitate reducing a risk of emboli in the bloodstream. Filler material 202 may include, for example, a bio-adhesive and/or porous polymeric material.

In the example embodiment, filler material 202 is coupled to and between second legs 124, such that filler material 202 is disposed within the PFO tunnel when medical device 108 is deployed. Filler material 202 may extend from inner reverse bends 118 to outer reverse bends 128, such that filler material 202 is coupled to and occupies substantially the entire second body plane 129. Filler material 202 may additionally be coupled to body 114 at other locations (e.g., between first legs 120 and/or between third legs 130).

Figure 18:
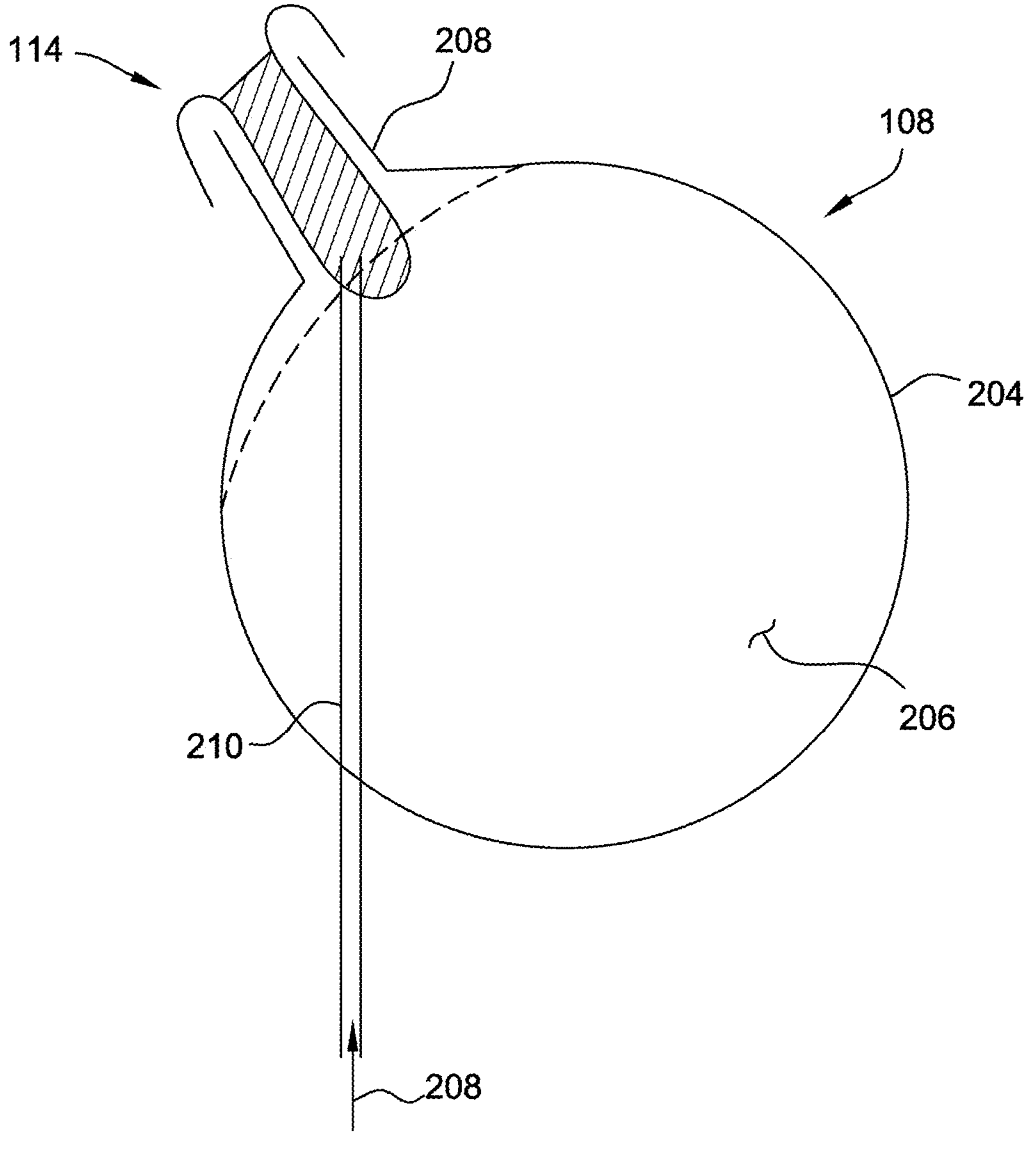
FIG. 18 depicts another embodiment of a medical device, including a fillable bag.

Another embodiment of a medical device 108 is shown in FIG. 18. In this embodiment, a bag 204 is coupled to body 114 of medical device 108. Bag 204 is coupled to body 114 at first legs 120 or second legs 124, and defines a cavity 206 therein. When medical device 108 is deployed in the PFO tunnel, a filler material 208 may be injected into bag 204 (e.g., through an inlet or lumen 210) to fill cavity 206 and inflate bag 204 within the PFO tunnel. In this way, bag 204 functions to fill the PFO tunnel, and may facilitate reducing a risk of emboli in the bloodstream. Bag 204 may be made of a non-porous polymeric material, or any other suitable material. In some embodiment, bag 204 is formed from a bioabsorbable material, when inflated and engaged with septum secundum 160 and septum primum 162, contacts septum secundum 160 and septum primum 162 to block blood flow therebetween. Filler material 208 may include any suitable material, such as saline.

Figure 19:
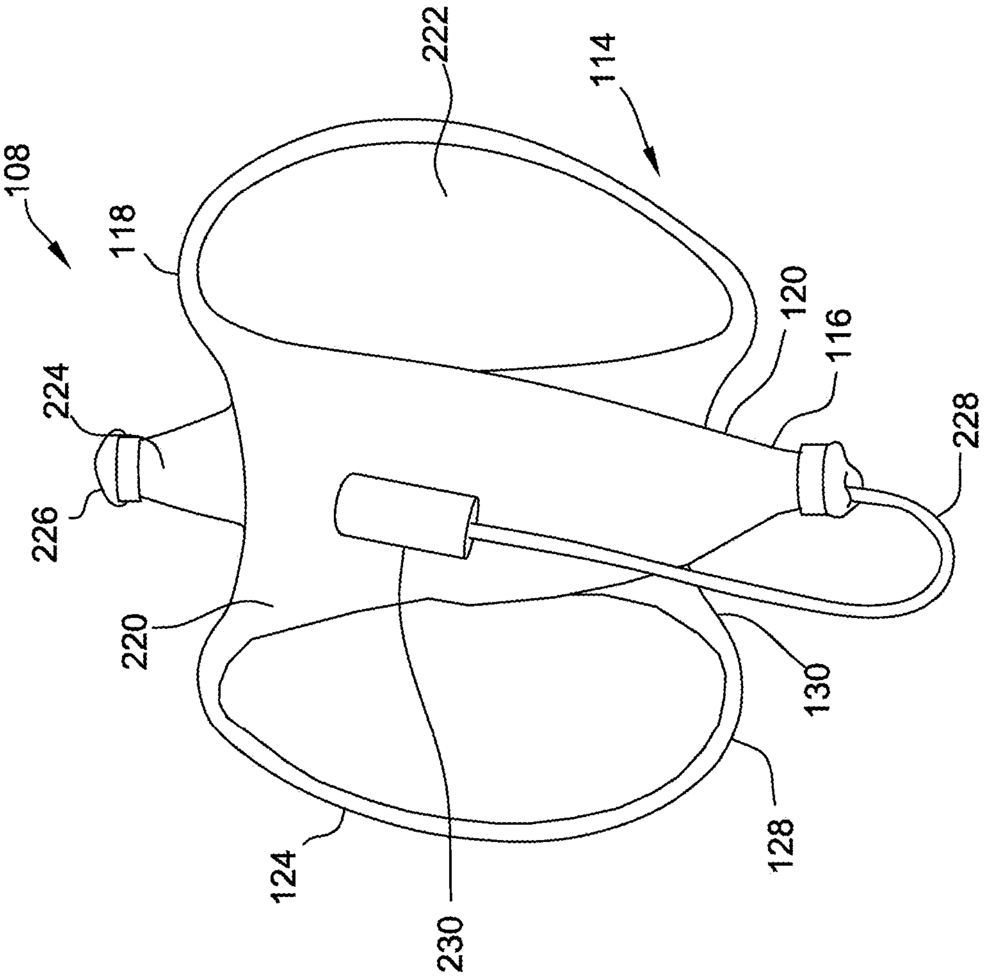
FIG. 19 is a front perspective view of yet another embodiment of a medical device, formed from a braided material.
Figure 20:
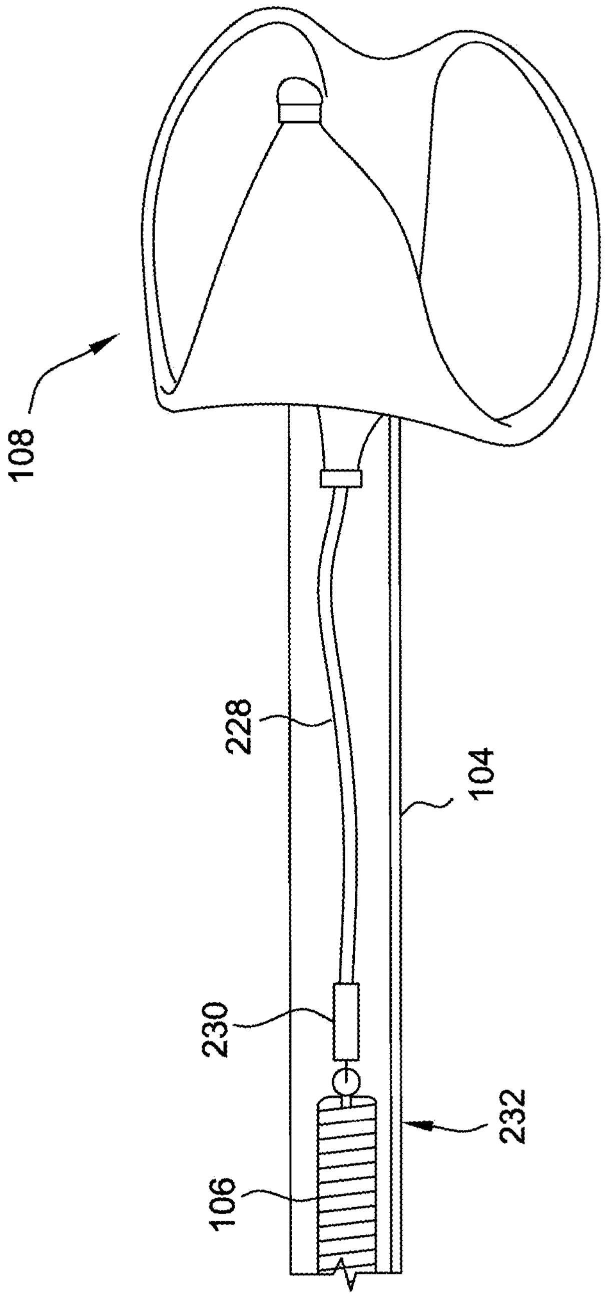
FIG. 20 illustrates the medical device shown in FIG. 19 deployed using the delivery system shown in FIG. 2.
Figures 30A, 30B, 30C:
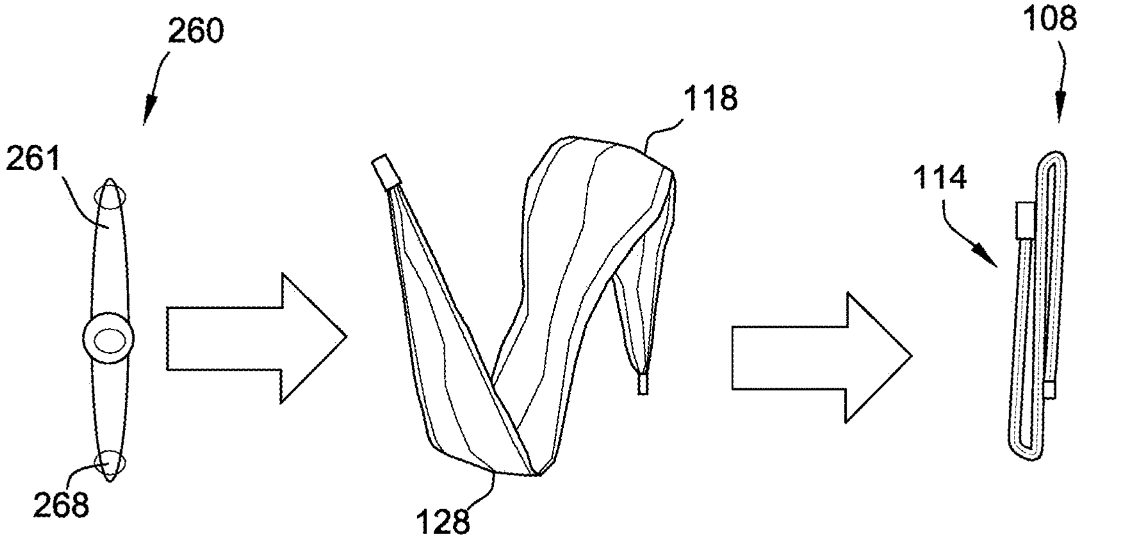
FIGS. 30A-30C depict forming a medical device from the blank shown in FIG. 29.
Figure 31A:
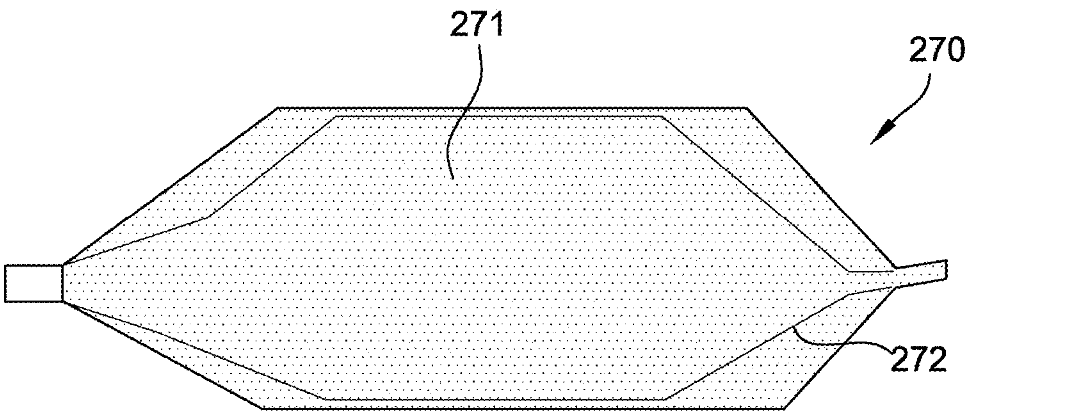
FIGS. 31A-31C depict alternative medical device blanks.
Figure 31B:
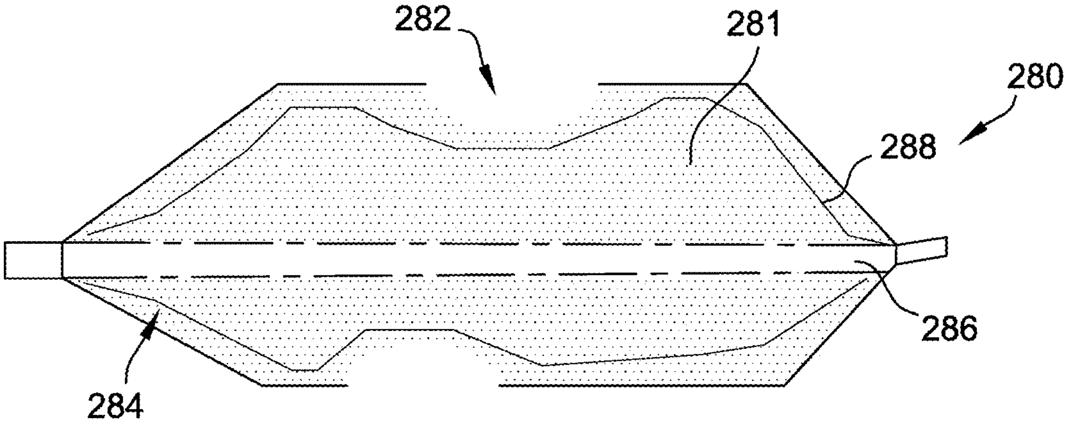
Figure 31C:
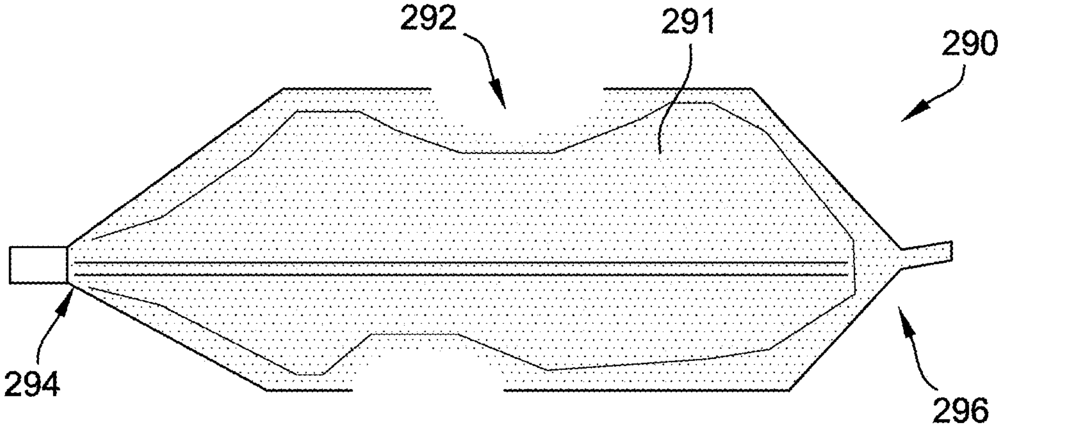

FIGS. 19-24 depict yet another embodiment of a medical device in accordance with the present disclosure. Specifically, FIG. 19 is a front perspective view of yet another embodiment of medical device 108, FIG. 20 illustrates medical device 108 deployed using delivery system 100 (shown in FIG. 2), and FIGS. 21A-24 depict medical device 108 deployed for closure of cardiac tissue (e.g., a PFO). In addition, FIGS. 25-30C illustrate blanks for forming medical devices and methods of forming such medical devices 108, and FIGS. 31A-31C illustrate variations of these medical devices 108.

In this embodiment, medical device 108—specifically body 114 thereof—is formed from a braided shaped-memory material (e.g., a braided nitinol fabric or other mesh material, such as PE, PET, Si, PLLA, PLGA, PlA, PLLA-PLC, etc.). In some such embodiments, the braided fabric has two layers, and an occlusive material (e.g., PET) is positioned between the two layers such that medical device 108 has an occlusive effect when deployed. In some embodiments, as described further herein, body 114 also includes a frame within the braided material, such as a wire frame, which may enhance the shape-memory characteristics of body 114 (e.g., the tendency to return to the expanded or final configuration). Central segment 116 is formed at free ends of the braided fabric (and/or free ends of the frame, where a frame is present), and may include a crimp, a weld, or other mechanical fastener to prevent the free ends from unraveling.

In this exemplary embodiment, medical device 108 may not include "legs" per se (e.g., first legs 120, second legs 124, and third legs 130 described above). Rather, body 114 includes a first body plane 220 of material defined between and extending from central segment 116 to a continuous inner reverse bend 118, and between "first legs 120" (e.g., edges of body 114 between central bend 116 and inner reverse bend 118), a second body plane 222 of material defined between and extending from inner reverse bend 118 to a continuous outer reverse bend 128, and between "second legs 124" (e.g., edges of body between inner reverse bend 118 and outer reverse bend 120), and a third body plane 224 of material defined between and extending from outer reverse bend 128 to a terminus 226 of body 114, and between "third legs 130" (e.g., edges of body 114 between outer reverse bend 120 and terminus 226). Body planes 220, 222, and 224 are similar to body planes 121, 129, and 131, respectively, as described herein.

In the exemplary embodiment, inner reverse bend 118 may not be "inner", or closer, transversely, to central segment 116 than outer reverse bend 128. Accordingly, inner reverse bend 118 may be referred to as first reverse bend 118, and outer reverse bend 128 may be referred to as second reverse bend 128.

Terminus 226 is formed at free ends of the braided fabric or nitinol (and/or free ends of the frame, where a frame is present) at the end of third body plane 224 opposite second reverse bend 128, and may include a crimp, a weld, suture (s), or other mechanical fastener to prevent the free ends from unraveling.

Figures 21A, 21B, 21C, 21D:
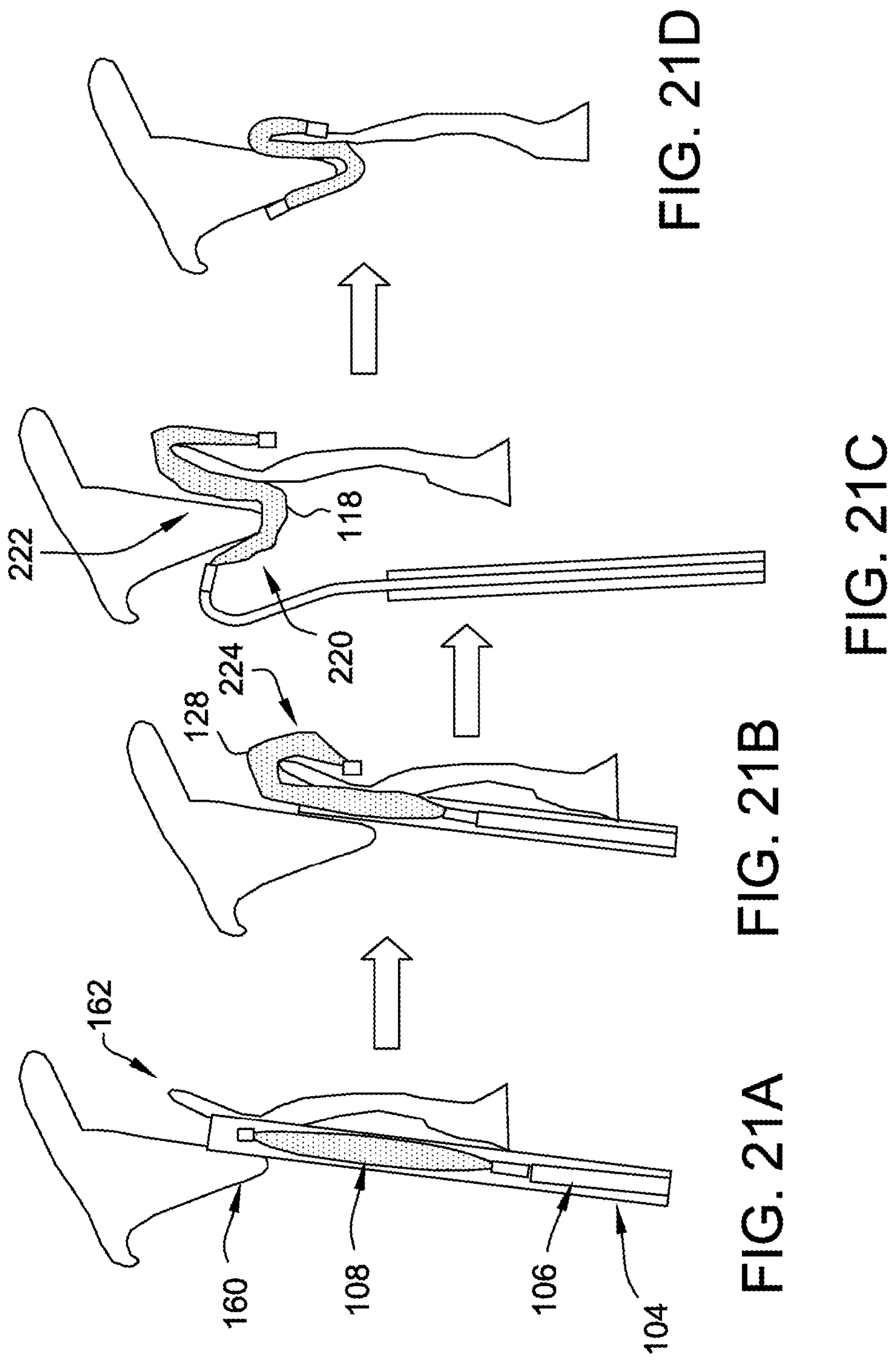
FIGS. 21A-21D depicts a method of deploying the medical device shown in FIG. 19.

In the illustrated embodiment, medical device 108 further includes an extension 228 extending from central segment 116. A coupling mechanism 230 is coupled to a free end of extension 228, and is configured to couple to a distal end 232 of delivery cable 106, as shown in FIG. 20. Medical device 108 may be deployed from delivery catheter 104 at a target location, as shown in FIGS. 21A-21D. Specifically, FIG. 21A illustrates medical device 108 initially coupled to delivery cable 106 within delivery catheter 104 and advanced to the target location (e.g., the PFO). Delivery catheter 104 is inserted between septum secundum 160 and septum primum 162.

Thereafter, as shown in FIG. 21B, medical device 108 is advanced distally out of delivery catheter 104. Based on the expanded or final (e.g., heat-set) configuration of medical device 108, third body plane 224 tends to extend downward as second reverse bend 128 is advanced from delivery catheter 104 and bend around the top edge of septum primum 162. Turning to FIG. 21C, medical device 108 is further advanced from delivery catheter 104. Second body plane 222 extends generally parallel to third body plane 224, between septum secundum 160 and septum primum 162. Based on the expanded or final (e.g., heat-set) configuration of medical device 108, first body plane 220 tends to extend upwards as first reverse bend 118 is advanced from delivery catheter 104 and bends around the bottom edge of septum secundum 160.

Figure 21F:
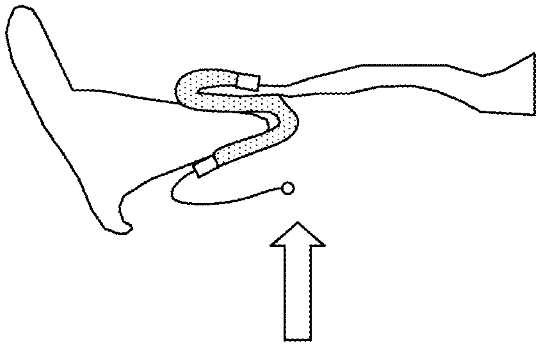
FIGS. 21E and 21F depict an alternative method of deploying the medical device shown in FIG. 19 including an extension.
Figure 21E:
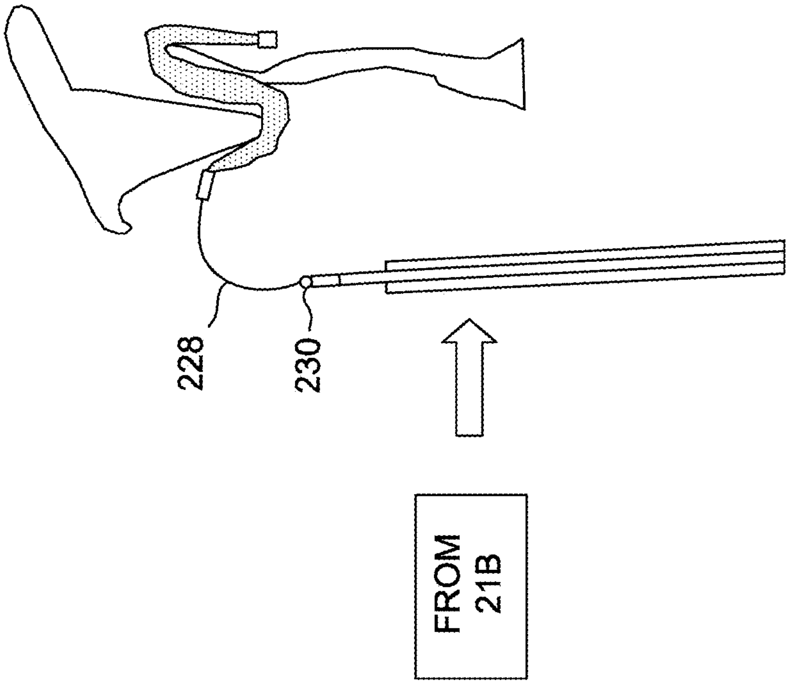

FIGS. 21E and 21F depict a similar alternative method of deployment of medical device 108, where medical device 108 includes extension 228 with coupling mechanism 230, as shown in FIG. 19. In this embodiment, the distal end of delivery cable 106 is coupled to coupling mechanism 230. Thereby, delivery cable 106 does not experience a sharp bend (e.g., as shown in FIG. 21C) to deploy medical device 108.

Figure 22:
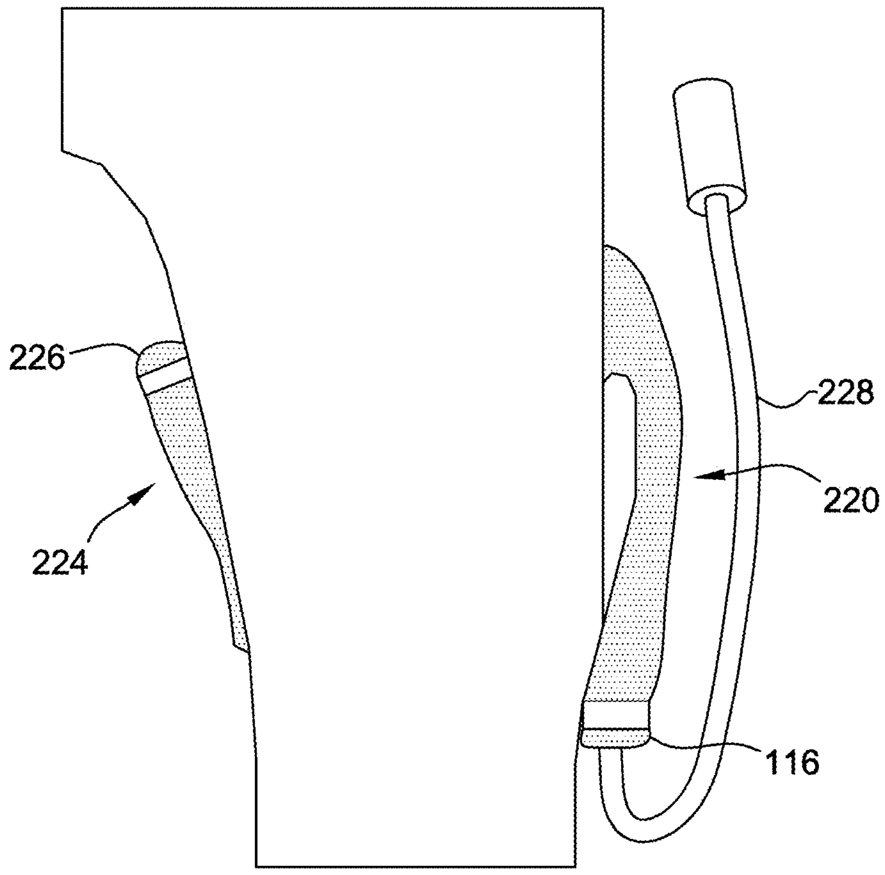
FIGS. 22-24 depict the medical device shown in FIG. 19 deployed for closure of cardiac tissue.
Figure 24:
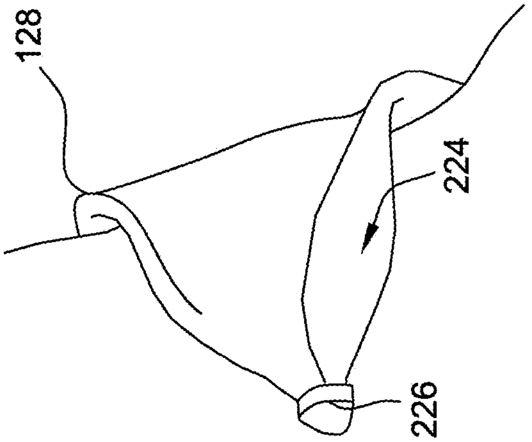
Figure 23:
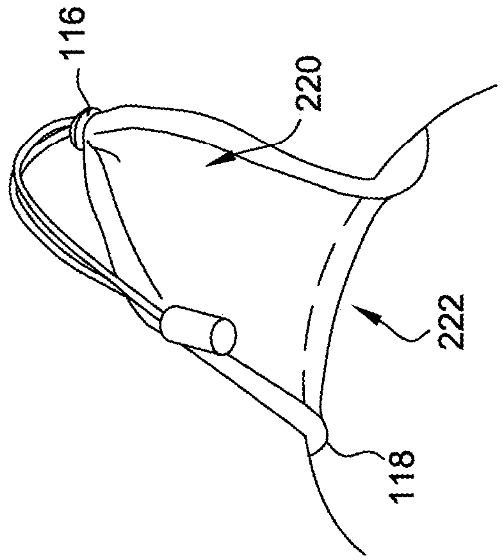

Once medical device 108 is in its fully deployed position, as shown in FIGS. 21D and 21F as well as in FIGS. 22-24, medical device 108 is detached from delivery cable 106. As described above, first reverse bend 118 engages the septum secundum 160, and second reverse bend 128 engages the septum primum 162. Moreover, first body plane 220 engages an outer surface of the septum secundum 160, second body plane 222 is positioned between and engages inner surfaces of the septum secundum 160 and the septum primum 162, and third body plane 224 engages the outer surface of the septum primum 162. This configuration allows for the septum secundum 160 and septum primum 162 to engage with each other and close the abnormality, allowing for proper blood flow during the cardiac cycle. Moreover, the braided material of body 114 further occludes and prevents blood flow between the septum secundum 160 and the septum primum 162. In some embodiments, this medical device 108 has a relatively small delivery profile compared to conventional PFO closure devices, such as less than 9 French, or as small as 4 French.

Figure 25:
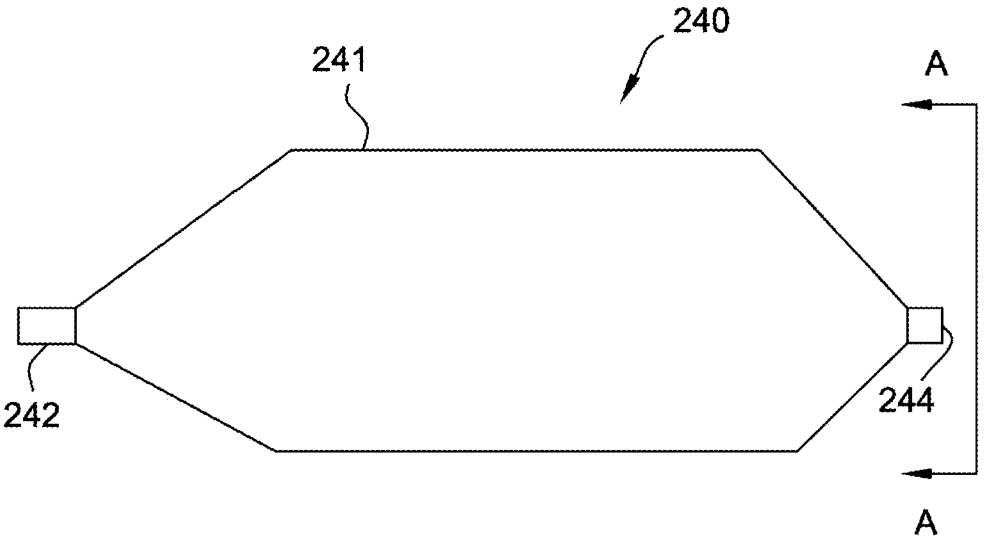
FIG. 25 depicts a medical device blank for forming a medical device according to the present disclosure.
Figures 26A, 26B, 26C:
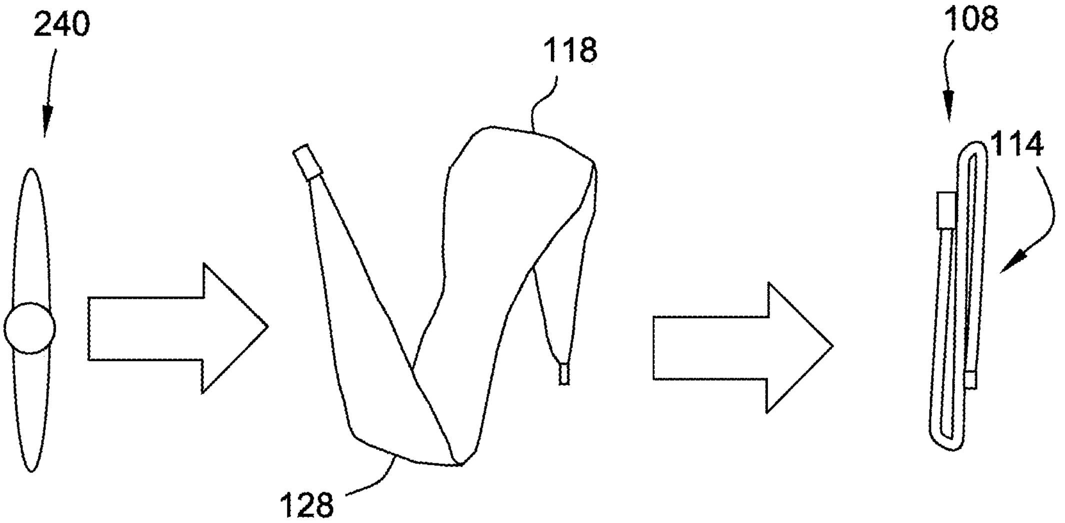
FIGS. 26A-26C depict forming a medical device from the blank shown in FIG. 25.

Blanks for forming medical devices and methods of forming medical devices in accordance with the present disclosure are shown in FIGS. 25-31C. Turning to FIG. 25, a pre-formed medical device blank 240 is depicted (e.g., for forming a medical device 108 as shown in FIGS. 19-24). Blank 240 includes a braided or mesh material 241, which forms body 114 (see FIG. 26C), with free ends welded or otherwise connected and terminated at a first juncture 242, representing central segment 116, and a second juncture 244, representing terminus 226. FIG. 26A depicts a longitudinal view of blank 240 taken along line A-A in FIG. 25. As shown in FIG. 26B, blank 240 is first bent and set (e.g., using a mandrel) to form first and second reverse bends 118, 128 of medical device 108, and may be further compressed into its final configuration (e.g., to form medical device 108), as shown in FIG. 26C.

Figure 27:
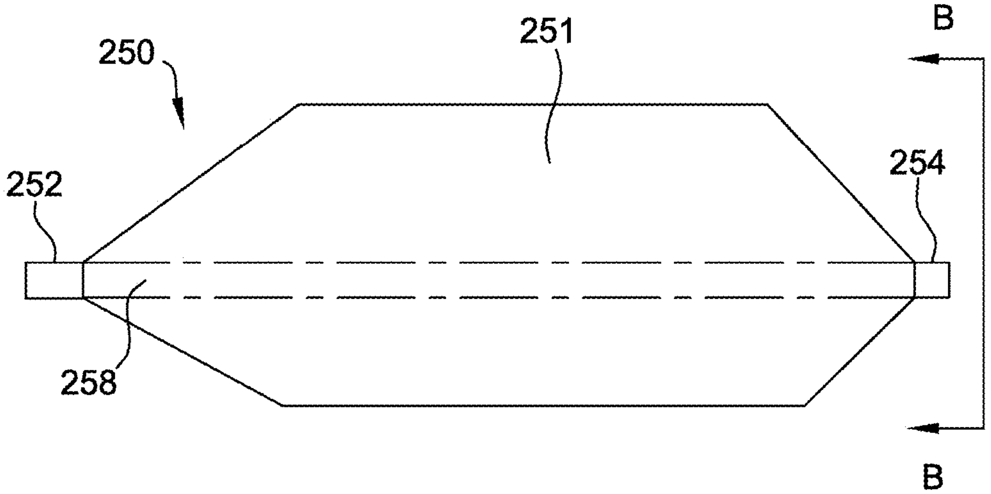
FIG. 27 depicts another embodiment of a medical device blank for forming a medical device according to the present disclosure.
Figures 28A, 28B, 28C:
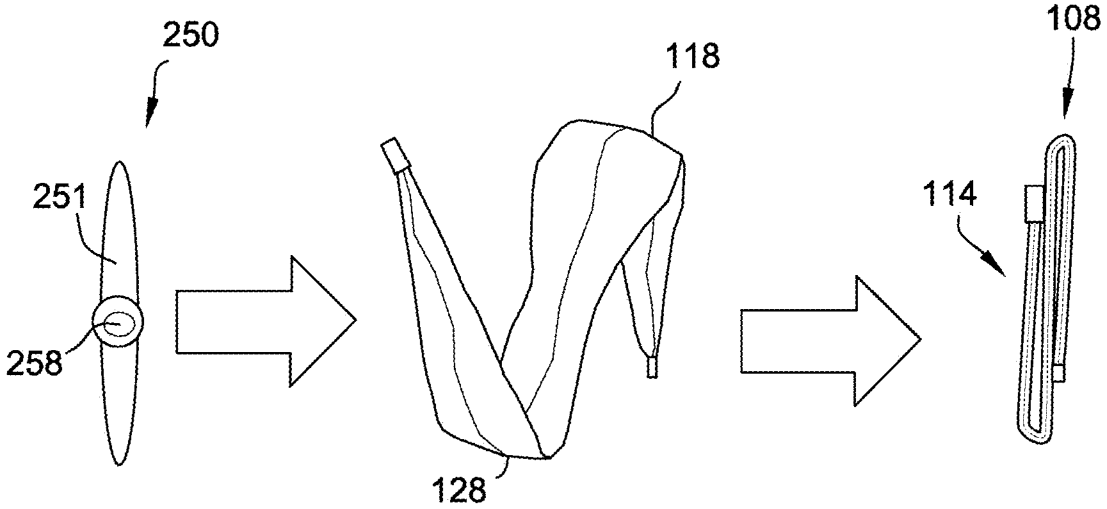
FIGS. 28A-28C depict forming a medical device from the blank shown in FIG. 27.

With reference now to FIG. 27, a pre-formed medical device blank 250 is depicted (e.g., for forming a medical device 108). Blank 250 includes a braided or mesh material 251, which forms body 114 (see FIG. 28C), with free ends welded or otherwise connected and terminated at a first juncture 252, representing central segment 116, and a second juncture 254, representing a terminus 226 (for example, as shown in FIG. 19). Blank 250 also includes a central wire 258 extending longitudinally therethrough and supporting the braided/mesh material 251. FIG. 28A depicts a longitudinal view of blank 250 taken along line B-B in FIG. 27. As shown in FIG. 28B, blank 250 is first bent and set (e.g., using a mandrel) to form first and second reverse bends 118, 128 of medical device 108. In this embodiment, both braided/mesh material 251 and central wire 258 are bent and set. Blank 250 may be further compressed into its final configuration (e.g., to form medical device 108), as shown in FIG. 28C.

Figure 29:
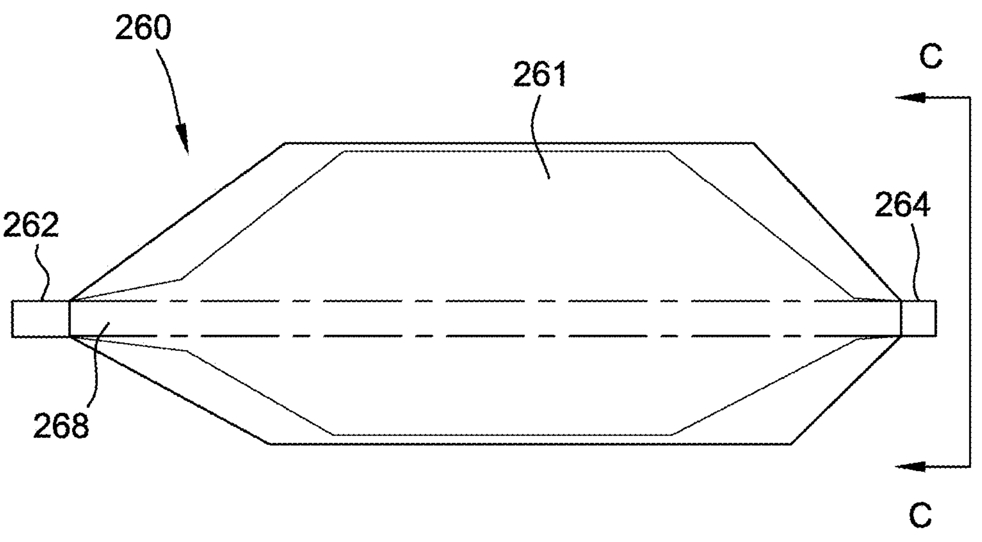
FIG. 29 depicts yet another embodiment of a medical device blank for forming a medical device according to the present disclosure.

With reference now to FIG. 29, a pre-formed medical device blank 260 is depicted (e.g., for forming a medical device 108). Blank 260 includes a braided or mesh material 261, which forms body 114 (see FIG. 30C), with free ends welded or otherwise connected at terminated at a first juncture 262, representing central segment 116, and a second juncture 264, representing a terminus 226 (for example, as shown in FIG. 19). Blank 260 also includes a wire frame 268 positioned within and supporting the braided/mesh material 261. FIG. 30A depicts a longitudinal view of blank 260 taken along line C-C in FIG. 29. As shown in FIG. 30B, blank 260 is first bent and set (e.g., using a mandrel) to form first and second reverse bends 118, 128 of medical device 108. In this embodiment, both braided/mesh material 261 and wire frame 268 are bent and set. Blank 260 may be further compressed into its final configuration (e.g., to form medical device 108), as shown in FIG. 30C.

FIGS. 31A-31C depict alternative blanks 270, 280, 290 for forming medical devices 108 as described herein. Specifically, FIG. 31A depicts a medical device blank 270 including a frame 272 formed from laser-cut material, frame 272 supporting braided/mesh material 271. Although frame 272 is illustrated as a single frame "cell", it is contemplated that frame 272 could include multiple cells. FIG. 31B depicts a medical device blank 280 in which the braided/mesh material 281 thereof is bowed or concave in a longitudinally central region 282 thereof. Blank 280 includes a wire frame 284 with a central wire 286 and a bowed or concave outer wire 288. Blank 280 may include multiple bowed and/or concave regions, which may aid in the formation of the reverse bends and/or facilitate improved (lateral) stretching of the PFO tunnel to keep the septum and primum taut, improving PFO tunnel closer. FIG. 31C depicts a medical device blank 290 in which the braided/mesh material 291 is bowed or concave in a longitudinally central region 292 thereof. An internal frame 294 is formed from multiple wires that are inverted at a distal end 296 of blank 290. Any of these blanks 270, 280, 290 can be bent and set as described above to form corresponding medical devices.

Figure 32:
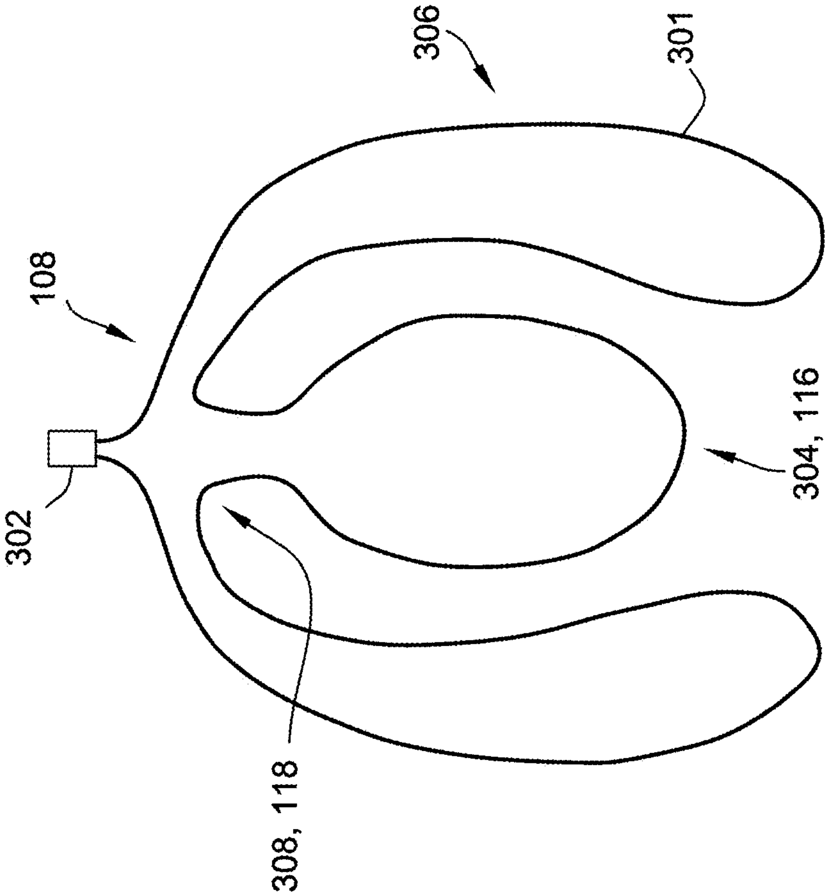
FIG. 32 depicts yet another embodiment of a medical device, formed from a single wire.
Figure 33:
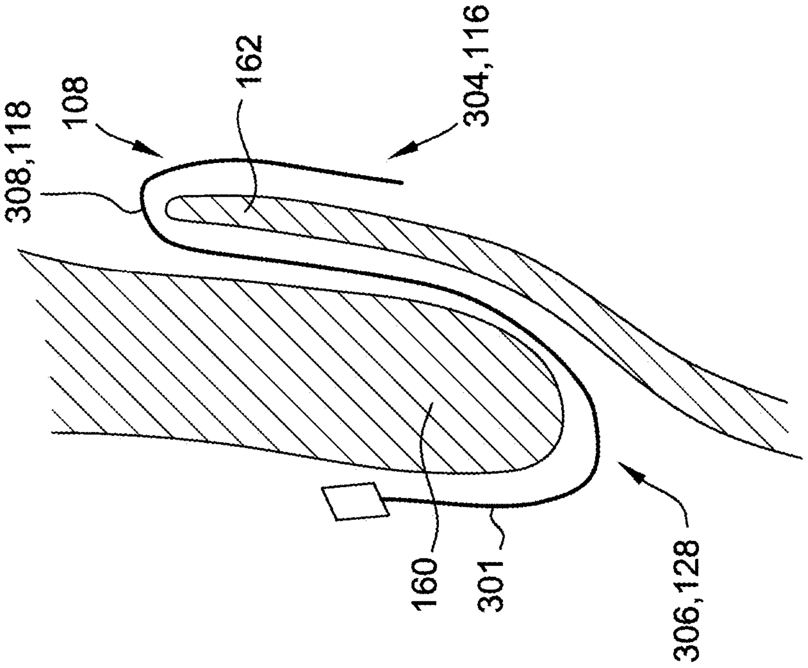
FIG. 33 depicts the medical device of FIG. 32 deployed for closure of cardiac tissue.

FIG. 32 depicts yet another embodiment of a medical device in accordance with the present disclosure, and FIG. 33 illustrates the medical device of FIG. 32 deployed in a PFO. This medical device 108 functions to hold septum secundum 160 and septum primum 162 together, as described elsewhere herein. However, in this embodiment, medical device 108 is formed from a continuous piece of wire 301, with free ends of the wire coupled together at a terminus 302 thereof (e.g., similar to terminus 226 shown in FIG. 19). Medical device 108 may be formed in a flat or two-dimensional configuration, as shown in FIG. 23, and bent and/or set into a final configuration for deployment in the PFO, as shown in FIG. 33. In the initial, flat configuration, the wire 301 forms a central region 304, which corresponds to central segment 116, and lateral regions 306, which are bent to form outer or second reverse bends 128. Inner or first reverse bends 118 are formed at a junction 308 between central region 304 and lateral regions 306. Although central region 304 is depicted with a rounded (e.g., circular or ellipsoidal) shape, central region 304 may be formed by bending the wire into alternative shapes, such a tiered or "beehive" shape, a "figure-8" shape, or any other suitable shape. These alternative shapes may reduce a load on central region 304 when medical device 108 is positioned within catheter 104 for deployment at the PFO. The overall size of medical device 108 may be dependent in part upon a diameter of the wire 301 selected to form medical device 108.

Figure 34:
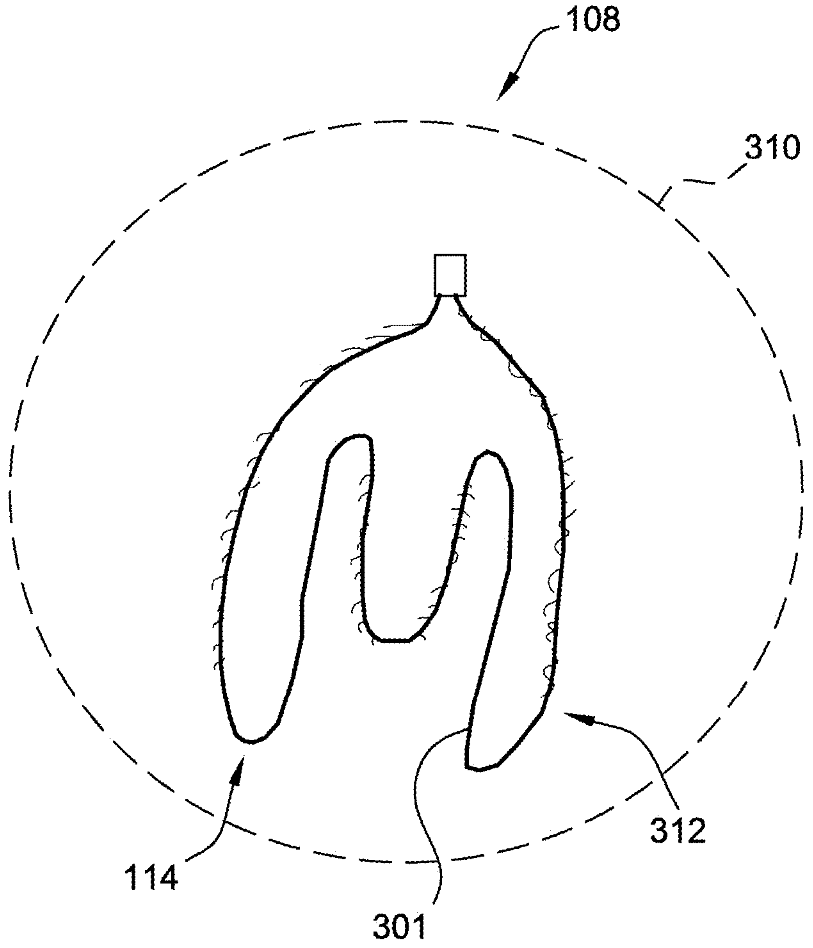
FIG. 34 depicts another embodiment of a medical device, including at least one patch.
Figure 36:
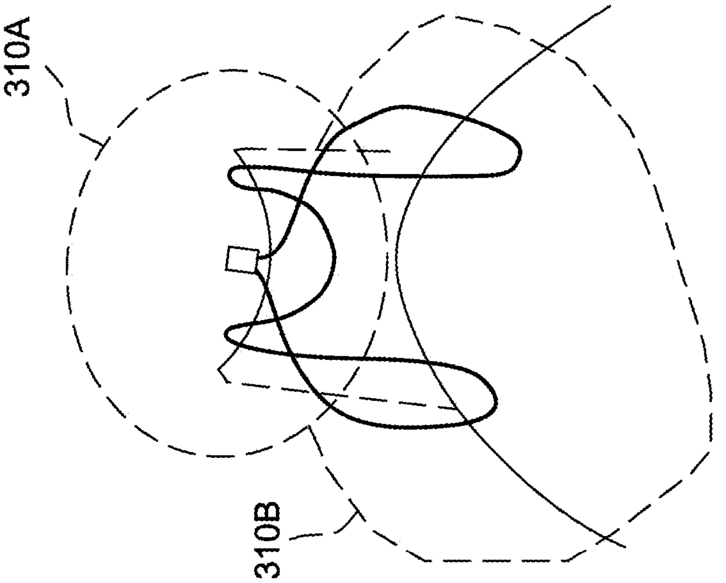
FIGS. 35 and 36 depict views of the medical device shown in FIG. 34 deployed for closure of cardiac tissue.
Figure 35:
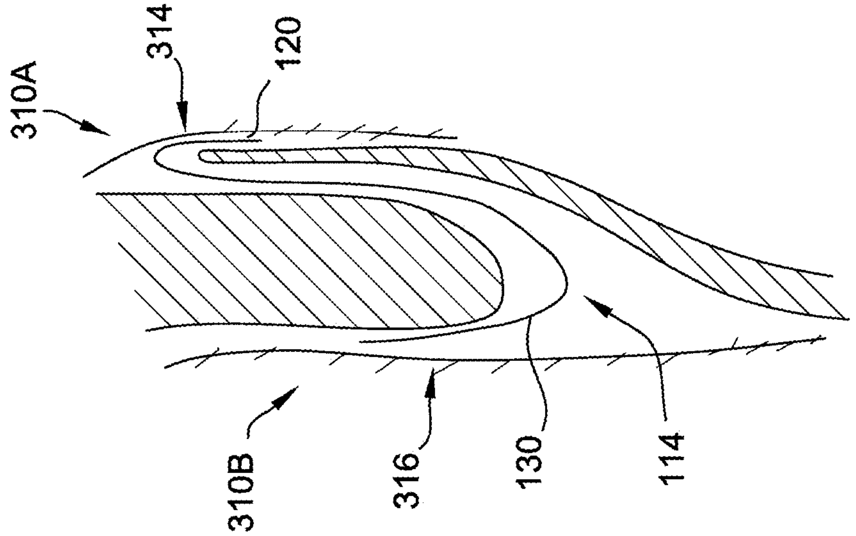

Turning to FIGS. 34-36, yet another embodiment of a medical device 108 is shown. In particular, medical device 108 includes at least one patch 310 coupled to body 114 thereof. Patch 310 is coupled to medical device body 114 using sutures 312. Alternatively, patch 310 is coupled to medical device body 114 using adhesive, one or more fasteners, welding, sealing, dip-molding to body 114, or any other suitable attachment method(s).

FIGS. 35 and 36 depict the medical device 108 of FIG. 34 deployed to close cardiac tissue (e.g., a PFO). Patch 310 is configured to engage cardiac tissue around medical device body 114, to seal PFO. In particular, patches 310 expand when medical device 108 is deployed, and about the cardiac wall to increase engagement of medical device 108 with the cardiac tissue and to facilitate sealing the PFO. In some embodiments, medical device 108 may include two patches 310, for deployment on either side of PFO. In such embodiments, a first patch 310A is coupled to central segment 116 and/or first legs 120 (e.g., to a first body plane 314, substantially similar to first body plane 121), and a second patch 310B is coupled to third legs 130 (e.g., to a third body plane 316, substantially similar to third body plane 131). In other embodiments, medical device 108 includes only one patch 310.

Patch 310 is formed from any suitable material including fabric, biocompatible fabric, biocompatible tissue, bio-adhesive material, or porous polymeric material. Moreover, although patch 310 is shown coupled to the medical device embodiment of FIG. 32 (e.g., formed from continuous wire 301), patch 310 can be used with any embodiment of medical device 108 disclosed herein. In addition, although patch 310 is illustrated as being larger than medical device body 114, in some embodiments, patch 310 is embodied as fabric/tissue patches that extend only between legs (e.g., first legs 120 or third legs 130) of the device body 114.

Figure 37:
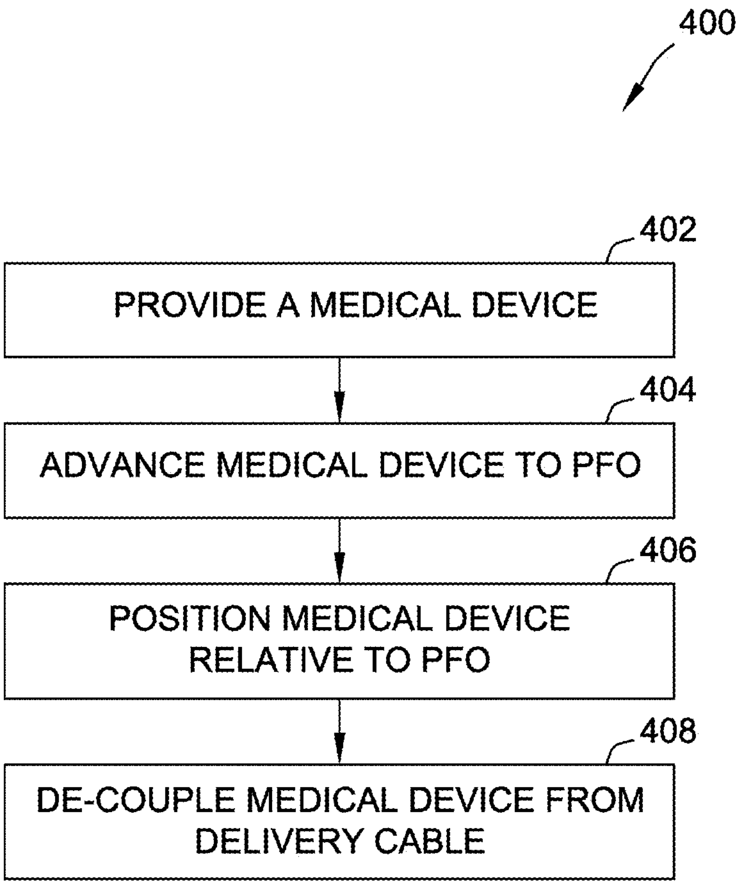
FIG. 37 is a flow diagram of an exemplary method of using a medical device to close a PFO.

FIG. 37 is a flow diagram of an exemplary method 400 of using medical device 108 to close a PFO in a patient. In the exemplary embodiment, method 400 includes providing 402 a medical device. As described herein, the medical device includes a first end, a second end, a central segment proximate a middle of the medical device and about which the medical device is symmetrical, a pair of inner reverse bends spaced from the central segment by a first body plane extending from the central segment to the pair of inner reverse bends in a first longitudinal direction, and a pair of outer reverse bends, wherein the pair of outer reverse bends are spaced from the pair of inner reverse bends by a second body plane extending from the pair of inner reverse bends to the pair of outer reverse bends in a second, opposite longitudinal direction, and wherein the pair of outer reverse bends are spaced from the first and second ends of the medical device by a third body plane extending in the first direction from the pair of outer reverse bends to the first and second ends.

Method 400 also includes advancing 404 the medical device to the PFO using a delivery system including a catheter and a delivery cable, positioning 406 the medical device relative to the PFO to secure a septum primum and septum secundum together, and decoupling 408 the medical device from the delivery cable to deploy the medical device.

Method 400 may include additional, alternative, and/or fewer steps, including those described herein. For example, in some embodiments, positioning 406 the medical device relative to the PFO includes positioning the first body plane of the medical device against the septum secundum, positioning the second body plane between the septum secundum and the septum primum, positioning the third body plane against the septum primum, positioning the pair of inner reverse bends against a top surface of the septum secundum, and/or positioning the pair of outer reverse bends against a bottom surface of the septum primum. Importantly, this can be performed in any suitable order, relative to how the device is deployed.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device comprising:

a body formed from a continuous braided shape memory fabric, the body comprising:

a central segment proximate a middle of the medical device;

a terminus proximate the middle of the medical device and spaced from the central segment in a depthwise direction by a depth;

a pair of inner reverse bends spaced from the central segment by a first body plane that is longitudinally defined between the central segment and the pair of inner reverse bends in a first longitudinal direction and laterally defined between first and second edges of the body; and a pair of outer reverse bends, wherein the pair of outer reverse bends are spaced from the pair of inner reverse bends by a second body plane that is longitudinally defined between the pair of inner reverse bends and the pair of outer reverse bends in a second, opposite longitudinal direction and laterally defined between the first and second edges of the body, and wherein the pair of outer reverse bends are spaced from the terminus of the medical device by a third body plane that is longitudinally defined between the pair of outer reverse bends and the terminus in the first longitudinal direction and laterally defined between the first and second edges of the body; and an extension having (i) a connected end connected to and extending from the central segment and (ii) a coupling mechanism at a free end of the extension, the coupling mechanism configured to enable coupling the medical device to a delivery cable for deployment of the medical device, wherein in a deployed condition of the medical device, the extension extends from the connected end in a first direction toward a bend, and in a second direction from the bend to the free end, the first direction being opposite the second end, wherein the medical device is a three-dimensional medical device, wherein first free strand ends of the braided shape memory fabric are coupled together at the central segment and opposite second free strand ends of the braided shape memory fabric are coupled together at the terminus, the braided shape memory fabric being continuous between the central segment and the terminus and between the first and second edges of the body.

2. The medical device of claim 1, wherein the first and second edges of the body define a pair of first legs extending between the central segment and the pair of inner reverse bends, the first body plane extending between the pair of first legs.

3. The medical device of claim 2, wherein the first and second edges of the body further define a pair of second legs extending between the pair of inner reverse bends and the pair of outer reverse bends, the second body plane extending between the pair of second legs.

4. The medical device of claim 3 wherein the first and second edges of the body further define a pair of third legs extending from the pair of outer reverse bends to the terminus of the medical device.

5. The medical device of claim 3, wherein the medical device is configured to be deployed to close a Patent Foramen Ovale (PFO), and, when the medical device is deployed, the pair of inner reverse bends are configured to engage a first surface of a septum secundum, the pair of first legs are configured to extend along the first surface of the septum secundum, the pair of second legs are configured to extend between the septum secundum and a septum primum, and the pair of outer reverse bends are configured to engage a first surface of the septum primum to hold the septum secundum and the septum primum together during a cardiac cycle.

6. The medical device of claim 1, wherein the medical device further comprises a frame within the braided shape memory fabric.

7. The medical device of claim 1, wherein the medical device is configured to be deployed to close a Patent Foramen Ovale (PFO), and, when the medical device is deployed, the first body plane is configured to engage a first surface of a septum secundum, the second body plane is configured to extend between the septum secundum and a septum primum, and the second body plane is configured to engage a first surface of the septum primum to hold the septum secundum and the septum primum together during a cardiac cycle.

8. The medical device of claim 7, wherein, when the medical device is deployed, the pair of inner reverse bends engage a top surface of the septum secundum and the pair of outer reverse bends engage a bottom surface of the septum primum.

9. The medical device of claim 1, wherein each of the first, second, and third body planes are different planes spaced from each other in the depthwise direction.

10. The medical device of claim 9, wherein each of the first, second, and third body planes are individually two-dimensional in shape.

11. The medical device of claim 1, wherein each of the central segment and the terminus includes a respective mechanical fastener configured to prevent the first free strand ends and the second free strand ends, respectively, from unravelling.

12. The medical device of claim 1, wherein a width of the second body plane is a maximum width of the body.

13. The medical device of claim 1, wherein the body further comprises an inner reverse edge and an outer reverse edge defined by the braided shape memory fabric, wherein the inner reverse edge comprises a bend or fold in the braided shape memory fabric that extends laterally between the pair of inner reverse bends and the outer reverse edge comprises a bend or fold in the braided shape memory fabric that extends laterally between the pair of outer reverse bends.

14. The medical device of claim 1, wherein the continuous braided shape memory fabric is a mesh material.

15. A delivery system for delivering a medical device to a target site, the delivery system comprising:

the medical device comprising a body formed from a continuous braided shape memory fabric, the body comprising: (i) a central segment proximate a middle of the medical device, (ii) a terminus proximate the middle of the medical device and spaced from the central segment in a depthwise direction by a depth, (iii) a pair of inner reverse bends spaced from the central segment by a first body plane that is longitudinally defined between the central segment and the pair of inner reverse bends in a first longitudinal direction and laterally defined between first and second edges of the body, and (iv) a pair of outer reverse bends, wherein the pair of outer reverse bends are spaced from the pair of inner reverse bends by a second body plane that is longitudinally defined between the pair of inner reverse bends and the pair of outer reverse bends in a second, opposite longitudinal direction and laterally defined between first and second edges of the body, and wherein the pair of outer reverse bends are spaced from the terminus of the medical device by a third body plane that is longitudinally defined between the pair of outer reverse bends and the terminus in the first longitudinal direction and laterally defined between first and second edges of the body, wherein the medical device is a three-dimensional medical device, wherein first free strand ends of the braided shape memory fabric are coupled together at the central segment and opposite second free strand ends of the braided shape memory fabric are coupled together at the terminus, the braided shape memory fabric being continuous between the central segment and the terminus and between the first and second edges of the body; and a delivery device coupled to the medical device, the delivery device comprising a catheter and a delivery cable, wherein the medical device is configured to coupled to the delivery cable, and wherein the delivery cable is configured to be advanced through the catheter to deploy the medical device at the target site, wherein the medical device include an extension having (i) a connected end connected to and extending from the central segment and (ii) a coupling mechanism at a free end of the extension, the coupling mechanism configured to couple the medical device to the delivery cable for deployment of the medical device, wherein in a deployed condition of the medical device, the extension extends from the connected end in a first direction toward a bend, and in a second direction from the bend to the free end, the first direction being opposite the second end.

16. The delivery system of claim 15, wherein the target site is a Patent Foramen Ovale (PFO), and wherein, when deployed, the medical device is configured to close the PFO by securing together a septum primum and a septum secundum of the PFO.

17. The delivery system of claim 15, wherein the catheter has an outer diameter of about 9 French.

18. The delivery system of claim 15, wherein the delivery cable is coupled to the central segment of the medical device.

19. A method for closing a Patent Foramen Ovale (PFO), the method comprising:

providing a medical device comprising a body formed from a continuous braided shape memory fabric, the body including: (i) a central segment proximate a middle of the medical device, (ii) a terminus proximate the middle of the medical device and spaced from the central segment in a depthwise direction by a depth, (iii) a pair of inner reverse bends spaced from the central segment by a first body plane that is longitudinally defined between the central segment and the pair of inner reverse bends in a first longitudinal direction and laterally defined between first and second edges of the body, and (iv) a pair of outer reverse bends, wherein the pair of outer reverse bends are spaced from the pair of inner reverse bends by a second body plane that is longitudinally defined between the pair of inner reverse bends and the pair of outer reverse bends in a second, opposite longitudinal direction and laterally defined between first and second edges of the body, and wherein the pair of outer reverse bends are spaced from the terminus of the medical device by a third body plane that is longitudinally defined between the pair of outer reverse bends and the terminus in the first longitudinal direction and laterally defined between first and second edges of the body, wherein the medical device is a three-dimensional medical device, wherein first free strand ends of the braided shape memory fabric are coupled together at the central segment and opposite second free strand ends of the braided shape memory fabric are coupled together at the terminus, the braided shape memory fabric being continuous between the central segment and the terminus and between the first and second edges of the body;

advancing the medical device to the PFO using a delivery system including a catheter and a delivery cable;

positioning the medical device relative to the PFO to secure a septum primum and septum secundum together; and de-coupling the medical device from the delivery cable to deploy the medical device, wherein the medical device include an extension having (i) a connected end connected to and extending from the central segment and (ii) a coupling mechanism at a free end of the extension, the coupling mechanism configured to couple the medical device to the delivery cable for deployment of the medical device, wherein after deploying the medical device, the extension extends from the connected end in a first direction toward a bend, and in a second direction from the bend to the free end, the first direction being opposite the second end.

20. The method of claim 19, wherein positioning comprises:

positioning the first body plane of the medical device against the septum secundum;

positioning the second body plane between the septum secundum and the septum primum; and placing the third body plane against the septum primum.

21. The method of claim 19, wherein positioning comprises:

positioning the pair of inner reverse bends against a top surface of the septum secundum; and positioning comprises positioning the pair of outer reverse bends against a bottom surface of the septum primum.

* * * * *